United States Patent
Gleave et al.

(10) Patent No.: US 9,095,602 B2
(45) Date of Patent: Aug. 4, 2015

(54) CHEMO- AND RADIATION-SENSITIZATION OF CANCER BY ANTISENSE TRPM-2 OLIGODEOXYNUCLEOTIDES

(71) Applicants: Martin Gleave, Vancouver (CA); Paul S. Rennie, Richmond (CA); Hideaki Miyake, Vancouver (CA); Colleen Nelson, Surrey (CA); Tobias Zellweger, Basel (CH)

(72) Inventors: Martin Gleave, Vancouver (CA); Paul S. Rennie, Richmond (CA); Hideaki Miyake, Vancouver (CA); Colleen Nelson, Surrey (CA); Tobias Zellweger, Basel (CH)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 13/737,630

(22) Filed: Jan. 9, 2013

(65) Prior Publication Data

US 2013/0143944 A1   Jun. 6, 2013

Related U.S. Application Data

(63) Continuation of application No. 12/431,997, filed on Apr. 29, 2009, now Pat. No. 8,361,981, which is a continuation of application No. 09/967,726, filed on Sep. 28, 2001, now Pat. No. 7,569,551.

(60) Provisional application No. 60/236,301, filed on Sep. 28, 2000.

(51) Int. Cl.

| C12N 15/113 | (2010.01) |
| A61K 31/7125 | (2006.01) |
| A61K 31/00 | (2006.01) |
| A61K 31/337 | (2006.01) |
| A61K 31/66 | (2006.01) |
| A61K 31/704 | (2006.01) |
| A61K 45/06 | (2006.01) |
| C07K 14/775 | (2006.01) |
| A61K 48/00 | (2006.01) |

(52) U.S. Cl.
CPC ............. *A61K 31/7125* (2013.01); *A61K 31/00* (2013.01); *A61K 31/337* (2013.01); *A61K 31/66* (2013.01); *A61K 31/704* (2013.01); *A61K 45/06* (2013.01); *C07K 14/775* (2013.01); *A61K 48/00* (2013.01)

(58) Field of Classification Search
None
See application file for complete search history.

(56) References Cited

U.S. PATENT DOCUMENTS

| 5,417,978 | A | 5/1995 | Tari et al. |
| 5,563,255 | A | 10/1996 | Monia et al. |
| 5,646,042 | A | 7/1997 | Stinchcomb et al. |
| 5,721,237 | A | 2/1998 | Myers et al. |
| 5,789,389 | A | 8/1998 | Tarasewitz et al. |
| 5,801,154 | A | 9/1998 | Baracchini et al. |
| 5,855,911 | A | 1/1999 | Lopez-Berestein et al. |
| 5,877,309 | A | 3/1999 | McKay et al. |
| 5,910,583 | A | 6/1999 | Marks et al. |
| 5,929,040 | A | 7/1999 | Werther et al. |
| 5,945,290 | A | 8/1999 | Cowsert et al. |
| 5,998,148 | A | 12/1999 | Bennett et al. |
| 6,111,094 | A | 8/2000 | Bennett et al. |
| 6,172,216 | B1 | 1/2001 | Bennett et al. |
| 6,335,194 | B1 | 1/2002 | Bennett et al. |
| 6,365,345 | B1 | 4/2002 | Brysch et al. |
| 6,383,808 | B1 | 5/2002 | Monia et al. |
| 6,451,991 | B1 | 9/2002 | Martin et al. |
| 6,900,187 | B2 | 5/2005 | Gleave et al. |
| 7,285,541 | B2 | 10/2007 | Gleave et al. |
| 7,368,436 | B2 | 5/2008 | Gleave et al. |
| 7,534,773 | B1 | 5/2009 | Gleave et al. |
| 7,569,551 | B2 | 8/2009 | Gleave et al. |
| 7,592,323 | B1 | 9/2009 | Gleave et al. |
| 7,732,422 | B2 | 6/2010 | Gleave et al. |
| 8,173,615 | B2 | 5/2012 | Gleave et al. |
| 8,361,981 | B2 | 1/2013 | Gleave et al. |
| 2003/0105051 | A1 | 6/2003 | McSwiggen |
| 2003/0158143 | A1 | 8/2003 | Gleave et al. |
| 2004/0006106 | A1 | 1/2004 | Uesugi et al. |
| 2004/0053874 | A1 | 3/2004 | Monia et al. |
| 2004/0096882 | A1 | 5/2004 | Gleave et al. |
| 2004/0220131 | A1 | 11/2004 | Jackson et al. |
| 2004/0224914 | A1 | 11/2004 | Jackson et al. |

(Continued)

FOREIGN PATENT DOCUMENTS

| WO | WO 99/51259 | 10/1999 |
| WO | WO 00/31048 | 2/2000 |

(Continued)

OTHER PUBLICATIONS

Agrawal et al., Antisense Therapeutics: is it as simple as complementary base recognition. Molecular Medicine Today, 2000, vol. 6, 72-81.

(Continued)

*Primary Examiner* — Tracy Vivlemore
(74) *Attorney, Agent, or Firm* — Larson & Anderson, LLC

(57) ABSTRACT

Administration of antisense oligodeoxynucleotides (ODN) targeted against the testosterone-repressed prostate message-2 (TRPM-2) gene can reduce the amount of TRPM-2 in renal cell cancer (RCC) cells and other cancer cells, and as a result enhance chemosensitivity of these cells to chemotherapy agents and radiation. Thus, for example, the sensitivity of renal cell cancer cells to a chemotherapeutic agent can be increased by exposing renal cell cancer cells to a chemotherapeutic agent and an agent which reduces the amount of TRPM-2 in the renal cell cancer cells. This provides an improved method for treatment of renal cell cancer, which is generally resistant to treatment with known chemotherapy agents.

12 Claims, 6 Drawing Sheets

(56) References Cited

U.S. PATENT DOCUMENTS

| | | |
|---|---|---|
| 2006/0024692 A1 | 2/2006 | Nakamura et al. |
| 2008/0014198 A1 | 1/2008 | Gleave et al. |
| 2008/0119425 A1 | 5/2008 | Gleave et al. |
| 2009/0258089 A1 | 10/2009 | Gleave et al. |
| 2011/0021603 A1 | 1/2011 | Gleave et al. |
| 2011/0142827 A1 | 6/2011 | Gleave et al. |
| 2012/0322850 A1 | 12/2012 | Gleave et al. |
| 2013/0017272 A1 | 1/2013 | Duksin et al. |
| 2013/0310440 A1 | 11/2013 | Duskin et al. |

FOREIGN PATENT DOCUMENTS

| | | |
|---|---|---|
| WO | WO 00/34469 | 6/2000 |
| WO | WO 01/46455 | 6/2001 |
| WO | WO 00/49937 | 8/2001 |
| WO | WO 01/01748 | 11/2001 |
| WO | WO 02/22635 | 3/2002 |
| WO | WO 02/50306 | 6/2002 |
| WO | WO 03/062421 | 7/2003 |
| WO | WO 03/072591 | 9/2003 |
| WO | WO 2004/018675 | 3/2004 |
| WO | WO 2004/018676 A2 | 3/2004 |
| WO | WO 2009/155381 | 12/2009 |
| WO | WO 2012/123820 | 9/2012 |
| WO | WO 2012/123823 | 9/2012 |
| WO | WO 2012/156817 | 11/2012 |
| WO | WO 2013/173757 | 11/2013 |

OTHER PUBLICATIONS

Branch, Andrea; A good Antisense Molecule is Hard to Find. TIBS, 1998, 45-50.
Crooke, Antisense Research and Application, Chapter 1, Springer-Verlag, New York. 1998.
Horoszewitcz et al., LNCaP Model of Human Prostatic Carcinoma. Cancer Research; Apr. 1983; 43:1809-1818.
Jen et al., Suppression of Gene Expression by Targeted Disruption of Messenger RNA: Available Options and Current Strategies. Stem Cells 2000; vol. 18, 307-319.
Opalinska et al., Nucleic-acid therapeutics: Basic principles and recent applications. Nature Reviews; 2002; vol. 1, 503-514.
Raghavan et al., Evolving Strategies of Cytotoxic Chemotherapy for Advanced Prostate Cancer. European Journal of Cancer.; 1997; vol. 33, No. 4 566-574.
Sensibar et al., Prevention of Cell Death Induced by Tumor Necrosis Factor alpha in LNCaP Cells by Overexpression of Sulfated Glycoprotein-2 (Clusterin). Cancer Research; Jun. 1, 1995; vol. 55; 2431-2437.
Agrawal et al., Importance of nucleotide sequence and chemical modifications of antisense oligonucleotides. Biochimica et Biophysica Acta 1489, 1999 53-68.
Bailey et al., Clusterin in the male reproductive system: localization and possible function. Molecular and Cellular Endocrinology, 1999, vol. 151 17-23.
Benner et al., Combination of Antisense Oligonucleotide and Low-Dose Chemotherapy in Hematological Malignancies. Journal of Pharmacological and Toxicological Method, 37:229-235; 1997.
Boral et al., Clinical Evaluation of Biologically Targeted Drugs: Obstacles and Opportunities. Cancer Chemother Pharmacol; vol. 42; 1998; S3-S21.
Bruchovsky et al., Control of tumor progression by maintenance of apoptosis. Prostate Suppl., 1996, 6:13-21.
Buttyan et al., Induction of the TRPM-2 Gene in Cells Undergoing Programmed Death. Molecular and Cellular Biology; Aug. 1989, vol. 9 No. 8 pp. 3473-3481.
Cox et al., Angiogenesis and Non-Small Cell Lung Cancer. Lung Cancer, vol. 27, 2000; 81-100.
Crooke et al., Basic Principles of Antisense Therapeutics, Antisense Research and Application. Springer, 2004; 1-50.
Darby et al., Vascular Expression of Clusterin in Experimental Cyclosporine Nephrotoxicity; Exp Nephrol; 1995; 3:234-239.

EMBL accession No. M63376, Jul. 1991.
Frieden et al., Expanding the design horizon of antisense oligonucleotides with alpha-L-LNA. Nucleic Acids Research; 2003, vol. 31, No. 6365-6372.
Genta Incorporated, New Data Reaffirm Genta's Molecular Target as Critical Factor for Enhancing Anticancer Treatment; www.genta.com 2001.
Gleave et al., Antisense Targets to Enhance Hormone and Cytocoxic Therapies in Advanced Prostate Cancer; Current Drug Targets; 2003; vol. 4, 209-221.
Gleave et al., Antisense therapy: Current status in prostate cancer and other malignancies. Cancer and Metastasis Reviews; 2002; Kluwer Academic Publishers; vol. 21, 79-92.
Gleave et al., Targeting anti-apoptotic genes upregulated by androgen withdrawal using antisense oligonucleotides to enhance androgen- and chemo-sensitivity in prostate cancer. Investigational New Drugs, 2002; Kluwer Academic Publishers; vol. 201 145-158.
Gleave et al., Use of Antisense Oligonucleotides Targeting The Antiapoptotic Gene Clusterin/Testosterone-Repressed Prostate Message 2, to Enhance Androgen Sensitivity and Chemosensistivity in Prostate Cancer. Elsevier Science Inc.; 39-49; 2001.
Ho et al., Lack of Association between Enhanced TRPM-2/Clusterin Expression and Increased Apoptotic Activity in Sex-Hormone-Induced Prostatic Dysplasia of the Noble Rat. American Journal of Pathology; Jul. 1998, vol. 153, No. 1, 131-139.
Jones et al., Molecules in focus Clusterin. The International Journal of Biochemistry and Cell Biology; 2002; vol. 34, 427-431.
Kadomatsu et al., Expression of sulfated glycoprotein 2 is associated with carcinogenesis induced by N-nitroso-N-methylurea in rat prostate and seminal vesicle. Cancer Research; Apr. 1, 1993; 53(7):1480-1483.
Kang et al., Antisense oligonucleotide of clusterin mRNA induces apoptotic cell death and prevents adhesion of rat ASC-17D sertoli cells. Molecules and Cells; Apr. 30, 2000. vol. 10, No. 2, 193-196.
Kirby et al., Bartonella-Associated Endothelial Proliferation Depends on Inhibition of Apoptosis. PNAS; vol. 99, No. 7; Apr. 2, 2002; 4656-4661.
Kyprianou et al., Bcl-2 Over-Expresion Delays Radiation-Induced Apoptosis without Affecting the Clonogenic Survival of Human Prostate Cancer Cells. Int J Cancer; Jan. 27, 1997; 70(3): 341-348.
Lee et al., In Vitro Models of Prostate Apoptosis: Clusterin as an Antiapoptotic Mediator. The Prostate Supplement; vol. 9; 21-24.
Manoharan, 2'-Carbohydrate modifications in antisense oligonucleotide therapy:importance of conformation, configuration, and conjugation. Biochimica et Biophysica Acta 1489 (1999) 117-130.
Metelev et al., Study of Antisense Oligonucleotide Phosphorothioates Containing Segments of Oligodeoxynucleotides and 2'-O-Methylogoribonucleotides. Bloorganic & Medicinal Chemistry Letters, 1994, vol. 4, No. 2 2929-2934.
Millar et al., Localization of mRNAs by in-situ hybridization to the residual body at stages IX-X of the cycle of the rat seminiferous epithelium: fact or artifact? International Journal of Andrology; 17:149-160.
Milner et al., Selecting effective antisense reagents on combinatorial oligonucleotide arrays. Nature Biotechnology; vol. 15; Jun. 1997; 531-541.
Miyake et al., Acquisition of chemoresistant phenotype by overexpression of the antiapoptotic gene testosterone-repressed prostate message-2 in prostate cancer. Cancer Research; May 1, 2000; vol. 60, 2547-2554.
Miyake et al., Antisense oligodeoxynucleotide therapy targeting clusterin gene for prostate cancer: Vancouver experience from discovery to clinic. International Journal of Urology; Sep. 2005; vol. 12 No. 9 785-794.
Miyake et al., Antisense TRPM-2 oligodeoxynucleotides Chemosensitize Human Androgen-independent PC-3 Prostate Cancer Cells Both in vitro and in vivo. Clinical Cancer Research; May 2000; vol. 6, 1655-1663.
Miyake et al., Novel Therapeutic strategy for advanced prostate cancer using antisense oligodeoxynucleotides targeting antiapoptotic genes upregulated after androgen withdrawal to delay androgen-

(56) References Cited

OTHER PUBLICATIONS independent progression and enhance chemosensitivity. International Journal of Urology; 2001; vol. 8, 337-349.
Miyake et al., Synergistic Chemsensitixation and Inhibition of Tumor Growth and Metastasis by the Antisense Oligodeoxynucleotide Targeting Clusterin Gene in a Human Bladder Cancer Model. Clinical Cancer Research; Dec. 2001; vol. 7, 4245-4251.
Miyake et al., Testosterone-repressed Prostate Message-2 is an Antiapoptotic Gene Involved in Progression to Androgen Independence in Prostate Cancer. Cancer Research 60; Jan. 1, 2000; 170-176.
Moulson et al., Clusterin (apoJ) regulates vascular smooth muscle cell differentiation in vitro. Journal of Cellular Physiology; 1999; vol. 180, 355-364.
Nor et al., Engineering and Characterization of Functional Human Microvessels in Immunodeficient Mice; Laboratory Investigation. vol. 81, No. 4; Apr. 2001; 453-463.
Nor et al., Up-Regulation of Bcl-2 in Microvasculat Endothelial Cells Enhances Intratumoral Angiogenesis and Accelerates Tumor Growth. Cancer Research; vol. 61; Mar. 1, 2001 2183-2188.
Rosenberg et al., Clusterin: Physiologic and Pathophysiologic Considerations. International Journal of Biochemistry; 1995; vol. 27 No. 7, 633-645.
Tran et al., A Role for Survivin in Chemoresistance of Endothelial Cells mediated by VEGF. PNAS; vol. 99, No. 7; Apr. 2, 2002; 4349-4354.
Wilson et al., Clusterin is a secreted mammalian chaperone. Frontlines; Mar. 2000; 95-98.
Wong et al., Molecular characterization of human TRPM-2/clusterin, a gene associated with sperm maturation, apoptosis and neurodegeneration. European Journal of Biochemistry; 1994; vol. 227, 917-925.
Wright et al., A ribonucleotide reductase inhibitor, MDL 101,731, induced apoptosis and elevates TRPM-2 mRNA levels in human prostate tumor xenografts. Exp Cell Res; Jan. 10, 1996; 222(1):54-60.
Yang et al., Nuclear Clusterin/XIP8, an x-ray-induced Ku70-binding protein that signals cell death. PNAS; vol. 97, Issue 11, 5907-5912; May 23, 2000.
Zangemeister-Wittke et al., A Novel Bispecific Antisense Oligonucleotide Inhibiting Both bcl-2 and bcl-xL Expression Efficiently Induces Apoptosis in Tumor Cells. Clinical Cancer Research; Jun. 2000; vol. 6, 2547-2555.
Zellweger et al., Antitumor Activity of Antisense Clusterin Oligonucleotides is Improved in vitro and in vivo by Incorporation of 2'-O-(2-Methoxy)Ethyl Chemistry. The Journal of Pharmacology and Experimental Therapeutics; Feb. 2001; vol. 298, No. 3, 934-940.
Zellweger et al., Chemosensitization of Human Renal Cell Cancer Using Antisense Oligonucleotides Targeting the Antiapoptotic Gene Clusterin. The Prostate Centre; 2001; vol. 3, No. 4 360-367.
Zwain at al., Clusterin Protects Granulosa Cells from Apoptotic Cell Death During Follicular Atresia. Experimental Cell Research; vol. 257; 2000; 101-110.
Rowinsky, The Development and Clinical Utility of the Taxane Class of Antimicrotubule Chemotherapy Agents. Annual Review of Medicine; 1997; vol. 48, 353-374.
Kurreck et al., Design of antisense oligonucleotides stabilized by locked nucleic acids. Nucleic Acids Research; 2002; vol. 30, No. 9, 1911-1918.
Chia et al., Phase II Trial of OGX-011 in Combination with Docetaxel in Metastatic Breast Cancer, Clin Cancer Res (2009) 15(2):708-13.
Gleave et al., Use of antisense oligonucleotides targeting the cytoprotective gene, clusterin, to enhance androgen- and chemo-sensitivity in prostate cancer. World J Urol (2005) 23: 38-46.
Kuriama, R., Effect of Taxol on First and Second Meiotic Spindle Formation in Ooctyes of the Surf Clam, *Spisula solidissima*. J. Cell Sci. (1986) 84:153-164.
Rowinsky et al., Taxol: A Novel Investigational Antimicrotuble Agent. Journal of the National Cancer Institute (1990) 82:1247-59.
Schiller at al., Comparison of Four Chemotherapy Regimens for Advanced Non-Small-Cell Lung Cancer. The New England Journal of Medicine (2002) 346:92-98.
So et al., Knockdown of the cytoprotective chaperone, clusterin, chemosensitizes human breast cancer cells both in vitro and in vivo. Mol. Cancer Thor. 4:1837-49.
Oct. 3, 2003 Office Action issued in connection with U.S. Appl. No. 09/913,325.
Oct. 30, 2003 Response filed in connection with U.S. Appl. No. 09/913,325.
Jan. 14, 2004 Office Action issued in connection with U.S. Appl. No. 09/913,325.
Jul. 19, 2004 Interview Summary and Supplemental Detailed Action issued in connection with U.S. Appl. No. 09/913,325.
Sep. 24, 2004 Response filed in connection with U.S. Appl. No. 09/913,325.
Oct. 29, 2004 Office Action issued in connection with U.S. Appl. No. 09/913,325.
Apr. 29, 2005 Response filed in connection with U.S. Appl. No. 09/913,325.
Jul. 28, 2005 Office Action issued in connection with U.S. Appl. No. 09/913,325.
Oct. 26, 2005 Response filed in connection with U.S. Appl. No. 09/913,325.
Jan. 12, 2006 Office Action issued in connection with U.S. Appl. No. 09/913,325.
Feb. 28, 2006 Response filed in connection with U.S. Appl. No. 09/913,325.
Mar. 30, 2006 Office Action issued in connection with U.S. Appl. No. 09/913,325.
Aug. 30, 2006 Response filed in connection with U.S. Appl. No. 09/913,325.
Nov. 14, 2006 Office Action issued in connection with U.S. Appl. No. 09/913,325.
Dec. 4, 2006 Interview Summary issued in connection with U.S. Appl. No. 09/913,325.
Jan. 3, 2007 Response filed in connection with U.S. Appl. No. 09/913,325.
Feb. 28, 2007 Office Action issued in connection with U.S. Appl. No. 09/913,325.
Mar. 21, 2007 Request for Continued Examination (RCE) and Amendment Accompanying RCE filed in connection with U.S. Appl. No. 09/913,325.
Jun. 14, 2007 Office Action issued in connection with U.S. Appl. No. 09/913,325.
Sep. 7, 2007 Response filed in connection with U.S. Appl. No. 09/913,325.
Nov. 27, 2007 Office Action issued in connection with U.S. Appl. No. 09/913,325.
Dec. 6, 2007 Response filed in connection with U.S. Appl. No. 09/913,325.
Mar. 21, 2006 Notice of Allowance issued in connection with U.S. Appl. No. 09/913,325.
Oct. 3, 2003 Office Action issued in connection with U.S. Appl. No. 09/944,326.
Oct. 30, 2003 Response filed in connection with U.S. Appl. No. 09/944,326.
Feb. 17, 2004 Office Action issued in connection with U.S. Appl. No. 09/944,326.
Jun. 17, 2004 Response filed in connection with U.S. Appl. No. 09/944,326.
Oct. 1, 2004 Office Communication issued in connection with U.S. Appl. No. 09/944,326.
Oct. 6, 2004 Response filed in connection with U.S. Appl. No. 09/944,326.
Oct. 29, 2004 Office Action issued in connection with U.S. Appl. No. 09/944,326.
Apr. 29, 2005 Response filed in connection with U.S. Appl. No. 09/944,326.
May 25, 2005 Office Action issued in connection with U.S. Appl. No. 09/944,326.
Jun. 26, 2005 Response filed in connection with U.S. Appl. No. 09/944,326.

(56) References Cited

OTHER PUBLICATIONS

Jul. 28, 2005 Office Action issued in connection with U.S. Appl. No. 09/944,326.
Sep. 28, 2005 Response filed in connection with U.S. Appl. No. 09/944,326.
Dec. 27, 2005 Office Communication issued in connection with U.S. Appl. No. 09/944,326.
Jan. 21, 2006 Response filed in connection with U.S. Appl. No. 09/944,326.
Apr. 4, 2006 Office Action issued in connection with U.S. Appl. No. 09/944,326.
May 29, 2006 Response filed in connection with U.S. Appl. No. 09/944,326.
Aug. 7, 2006 Office Action issued in connection with U.S. Appl. No. 09/944,326.
Aug. 21, 2006 Response filed in connection with U.S. Appl. No. 09/944,326.
Sep. 22, 2006 Office Action issued in connection with U.S. Appl. No. 09/944,326.
Dec. 1, 2006 Appeal Brief filed in connection with U.S. Appl. No. 09/944,326.
Mar. 19, 2007 Response filed in connection with U.S. Appl. No. 09/944,326.
Jun. 19, 2007 Response filed in connection with U.S. Appl. No. 09/944,326.
Sep. 4, 2007 Office Action issued in connection with U.S. Appl. No. 09/944,326.
Oct. 19, 2007 Response filed in connection with U.S. Appl. No. 09/944,326.
Nov. 29, 2007 Notice of Allowance issued in connection with U.S. Appl. No. 09/944,326.
Oct. 8, 2004 Notice of Allowance issued in connection with U.S. Appl. No. 10/080,794.
Jan. 31, 2011 Office Action issued in connection with U.S. Appl. No. 12/753,995.
Jun. 29, 2011 Response filed in connection with U.S. Appl. No. 12/753,995.
Sep. 20, 2011 Office Action issued in connection with U.S. Appl. No. 12/753,995.
Dec. 20, 2011 Response filed in connection with U.S. Appl. No. 12/753,995.
Jan. 6, 2012 Notice of Allowance issued in connection with U.S. Appl. No. 12/753,995.
Sep. 4, 2009 Office Action issued in connection with U.S. Appl. No. 11/875,226.
Nov. 2, 2009 Response filed in connection with U.S. Appl. No. 11/875,226.
Feb. 5, 2010 Notice of Allowance issued in connection with U.S. Appl. No. 11/875,226.
Feb. 8, 2011 Office Action issued in connection with U.S. Appl. No. 12/431,997.
Jul. 6, 2011 Response filed in connection with U.S. Appl. No. 12/431,997.
Sep. 22, 2011 Office Action issued in connection with U.S. Appl. No. 12/431,997.
Dec. 22, 2011 Response filed in connection with U.S. Appl. No. 12/431,997.
Jan. 6, 2012 Office Action issued in connection with U.S. Appl. No. 12/431,997.
Jan. 19, 2012 Response filed in connection with U.S. Appl. No. 12/431,997.
Feb. 2, 2012 Office Action issued in connection with U.S. Appl. No. 12/431,997.
Jul. 5, 2012 Response filed in connection with U.S. Appl. No. 12/431,997.
Sep. 7, 2012 Notice of Allowance issued in connection with U.S. Appl. No. 12/431,997.
Jul. 1, 2004 Office Action issued in connection with U.S. Appl. No. 09/967,726.
Jul. 28, 2004 Response filed in connection with U.S. Appl. No. 09/967,726.
Oct. 14, 2004 Office Action issued in connection with U.S. Appl. No. 09/967,726.
Nov. 26, 2004 Office Action issued in connection with U.S. Appl. No. 09/967,726.
Apr. 18, 2005 Response filed in connection with U.S. Appl. No. 09/967,726.
Jul. 13, 2005 Office Action issued in connection with U.S. Appl. No. 09/967,726.
Sep. 7, 2005 Response filed in connection with U.S. Appl. No. 09/967,726.
Sep. 23, 2005 Office Action issued in connection with U.S. Appl. No. 09/967,726.
Nov. 28, 2005 Appeal Brief filed in connection with U.S. Appl. No. 09/967,726.
Mar. 17, 2006 Office Action issued in connection with U.S. Appl. No. 09/967,726.
Jun. 16, 2006 Notice of Appeal and Appeal Brief filed in connection with U.S. Appl. No. 09/967,726.
Sep. 13, 2006 Examiner's Answer issued in connection with U.S. Appl. No. 09/967,726.
Oct. 12, 2006 Office Communication issued in connection with U.S. Appl. No. 09/967,726.
Oct. 25, 2006 Appeal Brief filed in connection with U.S. Appl. No. 09/967,726.
Nov. 9, 2006 Reply Brief filed in connection with U.S. Appl. No. 09/967,726.
Dec. 22, 2006 Office Communication issued in connection with U.S. Appl. No. 09/967,726.
Jan. 16, 2007 RCE and Amendment Accompanying RCE filed in connection with U.S. Appl. No. 09/967,726.
Apr. 9, 2007 Office Action issued in connection with U.S. Appl. No. 09/967,726.
May 1, 2007 Response filed in connection with U.S. Appl. No. 09/967,726.
Jul. 25, 2007 Office Action issued in connection with U.S. Appl. No. 09/967,726.
Dec. 18, 2007 Response filed in connection with U.S. Appl. No. 09/967,726.
Apr. 4, 2008 Office Action issued in connection with U.S. Appl. No. 09/967,726.
Jul. 3, 2008 Response filed in connection with U.S. Appl. No. 09/967,726.
Oct. 16, 2008 Notice of Allowance issued in connection with U.S. Appl. No. 09/967,726.
Apr. 4, 2008 Office Action issued in connection with U.S. Appl. No. 11/276,581.
Apr. 22, 2008 Response filed in connection with U.S. Appl. No. 11/276,581.
Aug. 19, 2008 Office Action issued in connection with U.S. Appl. No. 11/276,581.
Nov. 17, 2008 Response filed in connection with U.S. Appl. No. 11/276,581.
Feb. 19, 2009 Office Action issued in connection with U.S. Appl. No. 11/276,581.
May 19, 2009 Response filed in connection with U.S. Appl. No. 11/276,581.
Jun. 3, 2009 Notice of Allowance issued in connection with U.S. Appl. No. 11/276,581.
Feb. 1, 2005 Office Action issued in connection with U.S. Appl. No. 10/646,391.
Feb. 24, 2005 Response filed in connection with U.S. Appl. No. 10/646,391.
Apr. 8, 2005 Office Action issued in connection with U.S. Appl. No. 10/646,391.
Jul. 8, 2005 Response filed in connection with U.S. Appl. No. 10/646,391.
Sep. 7, 2005 Office Action issued in connection with U.S. Appl. No. 10/646,391.
Oct. 26, 2005 Response filed in connection with U.S. Appl. No. 10/646,391.

(56) References Cited

OTHER PUBLICATIONS

Nov. 10, 2005 Office Action issued in connection with U.S. Appl. No. 10/646,391.
Feb. 1, 2006 Appeal Brief filed in connection with U.S. Appl. No. 10/646,391.
Apr. 14, 2006 Office Action issued in connection with U.S. Appl. No. 10/646,391.
Jul. 12, 2006 Response filed in connection with U.S. Appl. No. 10/646,391.
Sep. 18, 2006 Office Action issued in connection with U.S. Appl. No. 10/646,391.
Oct. 3, 2006 Petition filed in connection with U.S. Appl. No. 10/646,391.
Nov. 20, 2006 Response filed in connection with U.S. Appl. No. 10/646,391.
Dec. 20, 2006 Office Action issued in connection with U.S. Appl. No. 10/646,391.
Jan. 26, 2007 Petition Decision issued in connection with U.S. Appl. No. 10/646,391.
Mar. 5, 2007 Office Action issued in connection with U.S. Appl. No. 10/646,391.
Mar. 28, 2007 Office Action issued in connection with U.S. Appl. No. 10/646,391.
Apr. 5, 2007 Response filed in connection with U.S. Appl. No. 10/646,391.
May 1, 2007 Office Action issued in connection with U.S. Appl. No. 10/646,391.
May 18, 2007 Response filed in connection with U.S. Appl. No. 10/646,391.
Jun. 19, 2007 Notice of Allowance issued in connection wits U.S. Appl. No. 10/646,391.
Aug. 21, 2007 Amendment After Allowance filed in connection with U.S. Appl. No. 10/646,391.
Apr. 19, 2007 Notice issued in connection with U.S. Appl. No. 11/470,331.
Apr. 26, 2007 Response filed in connection with U.S. Appl. No. 11/470,331.
Aug. 13, 2007 Petition Decision issued in connection with U.S. Appl. No. 11/470,331.
Oct. 3, 2007 Petition filed in connection with U.S. Appl. No. 11/470,331.
Oct. 25, 2007 Petition Decision issued in connection with U.S. Appl. No. 11/470,331.
Oct. 25, 2007 Suggested Restriction Requirement filed in connection with U.S. Appl. No. 11/470,331.
Mar. 23, 2009 Office Action issued in connection with U.S. Appl. No. 11/470,331.
Apr. 15, 2009 Response filed in connection with U.S. Appl. No. 11/470,331.
Jul. 2, 2009 Office Action issued in connection with U.S. Appl. No. 11/470,331.
Oct. 1, 2009 Response filed in connection with U.S. Appl. No. 11/470,331.
Mar. 18, 2010 Office Action issued in connection with U.S. Appl. No. 11/470,331.
Jun. 7, 2010 Response filed in connection with U.S. Appl. No. 11/470,331.
Jun. 29, 2010 Office Action issued in connection with U.S. Appl. No. 11/470,331.
Jan. 20, 2011 RCE and Amendment Accompanying RCE filed in connection with U.S. Appl. No. 11/470,331.
Oct. 9, 2008 Office Action issued in connection with U.S. Appl. No. 11/718,815.
Oct. 31, 2008 Response filed in connection with U.S. Appl. No. 11/718,815.
Nov. 20, 2008 Office Action issued in connection with U.S. Appl. No. 11/718,815.
Feb. 20, 2009 Response filed in connection with U.S. Appl. No. 11/719,815.
Mar. 30, 2009 Office Action issued in connection with U.S. Appl. No. 11/718,815.
May 29, 2009 Response filed in connection with U.S. Appl. No. 11/718,815.
Jun. 5, 2009 Office Action issued in connection with U.S. Appl. No. 11/718,815.
Sep. 30, 2009 Appeal Brief filed in connection with U.S. Appl. No. 11/718,815.
Oct. 20, 2009 Office Communication issued in connection with U.S. Appl. No. 11/718,815.
Dec. 14, 2009 Appeal Brief filed in connection with U.S. Appl. No. 11/718,815.
Jan. 22, 2010 Examiner's Answer issued in connection with U.S. Appl. No. 11/718,815.
Mar. 9, 2010 Office Communication issued in connection with U.S. Appl. No. 11/718,815.
Mar. 22, 2010 Reply Brief filed in connection with U.S. Appl. No. 11/718,815.
Apr. 6, 2010 Office Communication issued in connection with U.S. Appl. No. 11/718,815.
Oct. 12, 2010 Communication Concerning Abandonment filed in connection with U.S. Appl. No. 11/718,815.
Oct. 26, 2010 Notice of Abandonment issued in connection with U.S. Appl. No. 11/718,815.
Jun. 28, 2011 Office Action issued in connection with U.S. Appl. No. 12/886,027.
Jul. 21, 2011 Response filed in connection with U.S. Appl. No. 12/886,027.
Sep. 8, 2011 Office Action issued in connection with U.S. Appl. No. 12/886,027.
Jan. 9, 2012 Response filed in connection with U.S. Appl. No. 12/886,027.
Mar. 8, 2012 Office Action issued in connection with U.S. Appl. No. 12/886,027.
Jul. 9, 2012 RCE and Amendment Accompanying RCE filed in connection with U.S. Appl. No. 12/886,027.
Aug. 11, 2000 International Search Report issued in connection with PCT International Patent Application No. PCT/US00/04875.
Feb. 26, 2001 Written Opinion issued in connection with PCT International Patent Application No. PCT/US00/04875.
May 17, 2001 Preliminary Examination Report issued in connection with PCT International Patent Application No. PCT/US00/04875.
Mar. 20, 2001 filed in connection with PCT International Patent Application No. PCT/US00/04875.
Aug. 23, 2001 Statement of Proposed Amendments filed in connection with Australian Patent Application No. 36064/00.
Feb. 14, 2003 Examiner's Report issued in connection with Australian Patent Application No. 36054/00.
May 13, 2003 Statement of Proposed Amendments filed in connection with Australian Patent Application No. 36064/00.
Jun. 3, 2003 Examiner's report issued in connection with Australian Patent Application No. 36064/00.
Sep. 2, 2003 Statement of Proposed Amendments filed in connection with Australian Patent Application No. 36064/00.
Feb. 12, 2004 Letters Patent issued in connection with Australian Patent Application No. 36064/00.
Sep. 7, 2000 Notification of Entry into European Phase issued in connection with European Patent Application No. 00914710.9.
Mar. 20, 2002 European Search Report filed in connection with European Patent Application No. 00914710.9.
Sep. 1, 2005 Examination Report issued in connection with European Patent Application No. 00914710.9.
Dec. 30, 2005 Response filed in connection with European Patent Application No. 00914710.9.
May 2, 2006 Examination Report issued in connection with European Patent Application No. 00914710.9.
Aug. 11, 2006 Response filed in connection with European Patent Application No. 00914710.9.
Jan. 23, 2007 Examination Report issued in connection with European Patent Application No. 00914710.9.
Apr. 4, 2007 Response filed in connection with European Patent Application No. 00914710.9.

(56) References Cited

OTHER PUBLICATIONS

Apr. 18, 2007 Examination Report issued in connection with European Patent Application No. 00914710.9.
Jun. 1, 2007 Response filed in connection with European Patent Application No. 00914710.9.
Jan. 7, 2008 Decision to Grant European Patent issued in connection with European Patent Application No. 00914710.9.
Sep. 27, 2007 Examination Report issued in connection with Canadian Patent Application No. 2,371,814.
Mar. 27, 2008 Response filed in connection with Canadian Patent Application No. 2,371,814.
Feb. 1, 2010 Response filed in connection with Canadian Patent Application No. 2,371,814.
Apr. 4, 2009 Examination Report issued in connection with Canadian Patent Application No. 2,371,814.
Oct. 14, 2010 Examination Report issued in connection with Canadian Patent Application No. 2,371,814.
Apr. 14, 2011 Response filed in connection with Canadian Patent Application No. 2,371,814.
Feb. 24, 2012 Examination Report issued in connection with Canadian Patent Application No. 2,371,814.
May 24, 2012 Response filed in connection with Canadian Patent Application No. 2,371,814.
Nov. 27, 2012 Examination Report issued in connection with Canadian Patent Application No. 2,371,814.
English Language Translation of Feb. 19, 2010 Examination Report issued in connection with Japanese Patent Application No. 2000-600553.
English Language Translation of Oct. 29, 2010 Examination Report issued in connection with Japanese Patent Application No. 2000-600553.
Jan. 28, 2011 Response filed in connection with Japanese Patent Application No. 2000-600553.
May 20, 2011 Response filed in connection with Japanese Patent Application No. 2000-600553.
English Language Translation of Feb. 16, 2011 Examination Report issued in connection with Japanese Patent Application No. 2000-600553.
English Language Translation of Dec. 26, 2006 Examination Report issued in connection with Korean Patent Application No. 10-2001-7010946.
English Language Translation of Mar. 14, 2007 Examination Report issued in connection with Korean Patent Application No. 10-2001-7010946.
English Language Translation of Jul. 27, 2006 Examination Report issued in connection with Korean Patent Application No. 10-2001-7010946.
English Language Translation of Oct. 11, 2307 Certificate of Patent, issued in connection with Korean Patent Application No. 10-2001-7010946.
Sep. 26, 2006 Response filed in connection with Korean Patent Application No. 10-2001-7010946.
Jan. 25, 2007 Response filed in connection with Korean Patent Application No. 10-2001-7010946.
Feb. 27, 2007 Response filed in connection with Korean Patent Application No. 10-2001-7010946.
May 10, 2007 Response filed in connection with Korean Patent Application No. 10-2001-7010946.
English Language Translation of Mar. 22, 2007 Examination Report issued in connection with Korean Patent Application No. 10-2007-7004243.
English Language Translation of Oct. 15, 2007 Examination Report issued in connection with Korean Patent Application No. 10-2007-7004243.
English Language Translation of Jan. 10, 2008 Notice of Allowance issued in connection with Korean Patent Application No. 10-2007-7004243.
Jul. 20, 2007 Response filed in connection with Korean Patent Application No. 10-2007-7004243.
Nov. 14, 2007 Response filed in connection with Korean Patent Application No. 10-2007-7004243.
English Language Translation of Apr. 1, 2008 Certificate of Patent, issued in connection with Korean Patent Application No. 10-2007-7004243.
Jul. 1, 2002 Examination Report issued in connection with New Zealand Patent Application Publication No. 513757.
Oct. 8, 2003 Examination Report issued in connection with New Zealand Patent Application Publication No. 513757.
Aug. 18, 2004 Examination Report issued in connection with New Zealand Patent Application Publication No. 513757.
Sep. 24, 2003 Response filed in connection with New Zealand Patent Application Publication No. 513757.
Oct. 11, 2004 Response filed in connection with New Zealand Patent Application Publication No. 513757.
Apr. 7, 2005 Letters Patent issued in connection with New Zealand Patent Application Publication No. 513757.
English Language Translation of May 26, 2009 Examination Report issued in connection with Norwegian Patent Application No. 20014058.
Jul. 1, 2010 Examination Report issued in connection with Norwegian Patent Application No. 20014058, including English Language Translation.
Dec. 9, 2010 Examination Report issued in connection with Norwegian Patent Application No. 20014058, including English Language Translation.
Mar. 9, 2011 Response filed in connection with Norwegian Patent Application No. 20014058.
May 19, 2010 Response filed in connection with Norwegian Patent Application No. 20014058.
Dec. 22, 2003 International Search Report issued in connection with PCT International Patent Application No. PCT/CA03/01276.
Mar. 24, 2003 International Preliminary Examination Report issued in connection with PCT International Patent Application No. PCT/CA03/01276.
Jul. 9, 2007 Examination Report issued in connection with Australian Patent Application No. 2003258425.
Oct. 30, 2007 Examination Report issued in connection with Australian Patent Application No. 2003258425.
Oct. 15, 2007 Response filed in connection with Australian Patent Application No. 2003258425.
Jan. 22, 2008 Response filed in connection with Australian Patent Application No. 2003258425.
Dec. 13, 2010 Examination Report issued in connection with Canadian Patent Application No. 2,494,764.
Aug. 3, 2011 Examination Report issued in connection with Canadian Patent Application No. 2,494,764.
Jun. 13, 2011 Response filed in connection with Canadian Patent Application No 2,494,764.
Feb. 3, 2012 Response filed in connection with Canadian Patent Application No. 2,494,764.
Aug. 8, 2007 Examination Report issued in connection with European Patent Application No. 03792074.1.
Dec. 10, 2007 Response filed in connection with European Patent Application No. 03792074.1.
Nov. 30, 2009 Summons to Attend Oral Proceedings issued in connection with European Patent Application No. 03792074.1.
Jan. 13, 2010 Result of Consultation issued in connection with European Patent Application No 03792074.1.
English Language Translation of Sep. 11, 2009 Examination Report issued in connection with Japanese Patent Application No. 2005-501197.
English Language Translation of Jan. 22, 2010 Examination Report issued in connection with Japanese Patent Application No. 2005-501197.
Dec. 8, 2009 Response filed in connection with Japanese Patent Application No. 2005-501197, including English Language Translation of the claims.
May 24, 2010 Response filed in connection with Japanese Patent Application No. 2005-501197.
English Language translation of the Allowed Claims in connection with Japanese Patent Application No. 2005-501197.

(56) References Cited

OTHER PUBLICATIONS

Oct. 27, 2010 Response filed in connection with Korean Patent Application No. 10-2005-7002964.
Feb. 25, 2011 Office Action issued in connection with Korean Patent Application No. 10-2005-7002964, including English Language Translation.
Mar. 24, 2011 Response filed in connection with Korean Patent Application No. 10-2005-7002964.
May 25, 2011 Notice of Allowance issued in connection with Korean Patent Application No. 10-2005-7002964, including English Language Translation.
Apr. 12, 2006 Examination Report issued in response to New Zealand Patent Application No. 538288.
Feb. 25, 2008 Examination Report issued in response to New Zealand Patent Application No. 538288.
Aug. 18, 2006 Response filed in response to New Zealand Patent Application No. 538288.
Jul. 16, 2007 Response filed in response to New Zealand Patent Application No. 538288.
Feb. 29, 2008 Response filed in response to New Zealand Patent Application No. 538288.
Apr. 8, 2008 Notice of Acceptance issued in response to New Zealand Patent Application No. 538288.
Aug. 30, 2012 Office Action issued in connection with Norwegian Patent Application No. 20051426, including English Language Translation.
Mar. 1, 2012 Office Action issued in connection with Norwegian Patent Application No. 20051426, including English Language Translation.
May 21, 2012 Response filed in connection with Norwegian Patent Application No. 20051426.
Oct. 22, 2012 Response filed in connection with Norwegian Patent Application No. 20051426.
Oct. 4, 2006 International Preliminary Report on Patentability issued in connection with PCT International Application No. PCT/CA2005/000531.
Mar. 7, 2007 International Preliminary Report on Patentability issued in connection with PCT International Application No. PCT/CA2005/001775.
Feb. 23, 2006 written Opinion issued in connection with PCT International Application No. PCT/CA2005/001775.
May 31, 2010 Examiner's Report issued in connection with Australian Patent Application No. 2005309274.
May 23, 2011 Response filed in connection with Australian Patent Application No. 2005309274.
Jun. 2, 2011 Examiner's Report issued in connection with Australian Patent Application No. 2005309274.
Jun. 27, 2011 Response filed in connection with Australian Patent Application No. 2005309274.
Jul. 12, 2011 Notice of Acceptance issued in connection with Australian Patent Application No. 2005309274.
English Language Translation of Nov. 4, 2011 Official Action issued in connection with Japanese Patent Application No. 2007-541607.
Feb. 6, 2012 Response filed in connection with Japanese Patent Application No. 2007-541607.
Apr. 1, 2009 Communication issued in connection with European Patent Application No. 05810600.6.
Aug. 31, 2009 Response filed in connection with European Patent Application No. 05810600.6.
Oct. 22, 2010 Communication issued in connection with European Patent Application No. 05810600.6.
Feb. 16, 2011 Response filed in connection with European Patent Application No. 05810600.6.
December 20, 2011 Communication issued in connection with European Patent Application No. 05810600.6.
Apr. 10, 2012 Response filed in connection with European Patent Application No. 05810600.6.
May 7, 2012 Communication issued in connection with European Patent Application No. 05810600.6.

Jul. 11, 2012 Response filed in connection with European Patent Application No. 05810600.6.
Aug. 7, 2012 Supplemental Response filed in connection with European Patent Application No. 05810600.6.
Aug. 8, 2012 Supplemental Response filed in connection with European Patent Application No. 05810600.6.
Oct. 28, 2012 Communication issued in connection with European Patent Application No. 05810600.6.
Jan. 25, 2013 Response filed in connection with European Patent Application No. 05810600.6.
Dec. 21, 2012 Office Action issued in connection with U.S. Appl. No. 13/464,670.
Apr. 22, 2013 Response filed in connection with U.S. Appl. No. 13/464,670.
May 20, 2013 Notice of Allowance issued in connection with U.S. Appl. No. 13/464,670.
May 27, 2013 Response filed in connection with Canadian Patent Application No. 2,371,814.
Mar. 17, 2009 European Search Report issued in connection with European Patent Application No. 05810600.6.
Nov. 26, 2012 International Search Report issued in connection with PCT International Patent Application No. PCT/IB12/01085.
U.S. Appl. No. 13/896,737, filed May 17, 2013 (Duksin et al.).
Aoki et al., RNA Interference may be more potent than antisense RNA in human cancer cell lines.; Clinical and Experimental Pharmacology and Physiology.; 2003; 96-102.
Azzoli et al., American Society of Clinical Oncolocy Clinical Practice Guideline Update on Chemotherapy for Stage IV Non-Small-Cell Lung Cancer, Journal of Clinical Oncology (2009) 27(36):6251-66.
Carthew et al., Gene silencing by double-stranded RNA.; Current Opinions in Cell Biology.; 2001; vol. 13, 244-248.
Chi et al., A Phase I Pharmacokinetic and Pharmacodynamic Study of OGX-011, a 2'-Methoxyethyl Antisense Oligonucleotide to Clusterin, in Patients with Localized Prostate Cancer, Journal of the National Cancer Institute, (2005) vol. 97, No. 17. pp. 1287-1296.
Chi et al., A Phase I Pharmacokinetic and Pharmacodynamic Study of OGX-011, a 2'-Methoxyethyl Phosphorothioate Antisense to Clusterin, in Combination with Docetaxel in Patients with Advanced Cancer, Clin Cancer Res (2008) 14(3):833-39.
Chi et al., Randomized Phase II Study of Docetaxel and Prednisone With or Without OGX-011 in Patients with Metastatic Castration-Resistant Prostate Cancer. Journal of Clinical Oncology (2010) 28:4247-54.
Chia et al., Phase II Trial of OGX-011 in Combination with Docetaxel in Metastatic Breast Cancer. Clin Cancer Res (2009) 15(2):708-13.
Chung et al., Enhanced chemosensisitivity of bladder cancer cells to ciplatin by suppression of clusterin in vitro.; Cancer Letters; Jan. 2004; vol. 203, No. 2, 155-161.
D'Addario et al., Practice Guidelines for diagnosis, treatment and follow-up. Annals of Oncology (2010) 21 (Supplement 5): v116-v119.
Dean et al., Antisense oligonucleotide-based therapeutics for cancer.; Oncogene; 2003; vol. 22, No. 56, 9087-9096.
Fidias and Novello, Strategies for Prolonged Therapy in Patients with Advanced Non-Small Cell Lung Cancer. Journal of Clinical Oncology (2010) 28(34):5116-23.
Fire et al., Potent and specific genetic interference by double-stranded RNA in Caenorhabdis elegans. Nature, 1998; vol. 391, 806-811.
Gewirtz, A critical evaluation of the mechanisms of action proposed for the antitumor effects of the anthracycline antibiotics adriamycin and daunorubicin.; Biochemical Pharmacology; 1999; vol. 57 727-741.
Gleave et al., Clusterin and IGFBPS AS Antisense Targets in Prostate Cancer. Annals of the New York Academy of Sciences, 2003; 95-104.
Gleave et al., Use of antisense oligonucleotides targeting the cytoprotective gene, clusterin, to enhance androgen- and chemo-sensitivity in prostate cancer. World J Urol, 2005, 23: 38-46.
Jemal et al., Global Cancer Statistics. CA Cancer J Clin, 2011, vol. 00, No. 0 pp. 1-22.

(56) References Cited

OTHER PUBLICATIONS

July et al., Clusterin expression is significantly enhanced in prostate cancer cells following androgen withdrawal therapy; The Prostate; 2002; vol. 50, 179-188.
July et al., Nucleotide-based therapies targeting clusterin chemosensitize human lung adenocarcinoma cells both in vitro and in vivo.; Molecular Cancer Therapeutics.; 2004, vol. 3, No. 3, 233-232.
Knox et al., Mechanism of Cytotoxicity of Anticancer Platinum Drugs: Evidence that cis-Diamminedichloroplatinum(II) and cis-Diammine-(1,1-cyclobutanedicarboxylato)platinum(II) Differ Only in the Kenetics of their Interaction with DNA. Cancer Research (1986) 46:1972-1979.
Kuriama, R., Effect of Taxol on First and Second Meiotic Spindle Formation in Ooctyes of the Surf Clam, *Spisula solidissima*. J. Cell Sol. (1986) 84:153-164.
Langer et al., The Evolving Role of Histology in the Management of Advanced Non-Small-Cell Lung Cancer. Journal of Clinical Oncology (2010) 28(38):5311-20.
Macfarlane at al., Research in castration-resistant prostate cancer: what does the future hold? Curr Oncol. (2010) vol. 17, Suppl. 2: S80-S86.
Massarelli et al., A retrospective analysis of the outcome of patients who have received two prior chemotherapy regimens including platinum and docetaxel for recurrent non-small-cell lung cancer. Lung Cancer (2003) 39:55-61.
Matsumoto et al., An evaluation of clusterin antisense inhibitor OGX-011 in combination with the second-generation antiandrogen MDV3100 in a castrate-resistant prostate model. 2011 ASCO Annual Meeting J Clin Oncol 29: 2011 (suppl; abstract No. 4502).
Millis et al., Clusterin Regulates Vascular Smooth Muscle Cell Nodule Formation and Migration.; Journal of Cellular Physiology; 2001; vol. 186, 201-219. Publisher: Wiley-Liss, Inc.
Miyake et al., Overexpression of clusterin in transitional cell carcinoma of the bladder is related to disease progression and recurrence; Urology; 2002; vol. 59, No. 1, 150-154.
National Comprehensive Cancer Network Clinical Practice Guidelines in Oncology, Non-Small Cell Lung Cancer. (Ettinger et al.) (2010) V.2.2010.
NCI Drug Dictionary. Cabazitaxel [online] Sep. 24, 2009 [retrieved Nov. 9, 2012]. Available on the internet:<URL:http://web.archive.org.web/20090925084202/http://www.cancer.gov/drugdictionary/?CrdID=534131>.
NCBI sequence accession No. NM_001831, O'Brien (1990).
Panico et al., Clusterin (CLU) and Lung Cancer. Adv Cancer Res 2009 vol. 105 pp. 63-76.
Pirker et al., Cetuximab plus chemotherapy in patients with advanced non-small-cell lung cancer (FLEX): an open-label randomised phase III trial. Lancet (2009) 373:1525-31.
Redondo et al., Overexpression of clusterin in human breast carcinoma.; American Journal of Pathology; Aug. 2000; vol. 157, No. 7, 393-399.
Rowinaky et al., The development of a clinical utility of the taxane class of antimicrotubile chemotherapy agents. 1997, 48:353-74.
Saijo et al., Pharmokinetics, Tissue Distribution, and Stability of Antisense Oligodeoxynucleotide Phosphorothioate., ISIS 3466 in Mice.; Oncology Research; 1994; Vo. 6 No. 6, 243-249.
Sandler et al., Paclitaxel-Carboplatin Alone or with Bevacizumab for Non-Small-Cell Lung Cancer. The New England Journal of Medicine (2006) 355:2542-50.
Schiller et al., Comparison of Four Chemotherapy Regimens for Advanced Non-Small-Cell Lung Cancer. The New England Journal of Medicine (2002) 346:92-98.
So et al., Knockdown of the cytoprotective chaperone, clusterin, chemosensitizes human breast cancer cells both in vitro and in vivo. Mol. Cancer Ther. 4:1837-49.
Teicher et al., Influence of Schedule on Alkylating Agent Cytotoxicity in Vitro and in Vivo. Cancer Research (1989) 46:5994-98.
Telford et al., Comparative evaluation of several DNA binding dyes in the detection of apoptosis-associated chromatin degradation by flow cytometry.; Cytometry; 1992; vol. 13, 137-143.
Trougakos et al., (2004) Silencing expression of the clusterin/apolipoprotein j gene in human cancer cells using small interfering RNA induces spontaneous apoptosis, reduced growth ability, and cell sensitization to genotoxic and oxidative stress. Cancer Research, 64(5):1834-42.
Zellweger et al. (2002) Enhanced Radiation sensitivity in prostate cancer by inhibition of the cell survival protein clusterin. Clinical Cancer Research (B):3276-3284.
Zoubeidi et al., Targeting the cytoprotective chaperone, clusterin, for treatment of advanced cancer. Clin Cancer Res. (2010) 16(4):1088-1093.
Levin, "A review of issues in the pharmacokinetics and toxicology of phosphorothioate antisense oligonucleoides," Biochimica at Biophysica Acta 1489:69-84 (1999).
Summerton, "Morpholino antisense oligomers: the case for an RNase H-independent structural type," Biochimica et Biophysica Acta 1489:141-158 (1999).
Wahlestedt et al., "Potent and nontoxic antisense oligonucleotides containing locked nucleic acids," PNAS 97 (10) :5633-5638 (2000).

| | |
|---|---|
| 1 | no treatment |
| 2 | antisense Clusterin ODN only |
| 3 | mismatch control ODN only |
| 4 | Taxol only |
| 5 | antisense Clusterin ODN + Taxol |
| 6 | mismatch control ODN + Taxol |

CHEMO- AND RADIATION-SENSITIZATION OF CANCER BY ANTISENSE TRPM-2 OLIGODEOXYNUCLEOTIDES

STATEMENT OF RELATED APPLICATIONS

This application is a continuation of U.S. Ser. No. 12/431,997, filed Apr. 29, 2009, a continuation of U.S. Ser. No. 09/967,726, filed Sep. 28, 2001, now U.S. Pat. No. 7,569,551, issued Aug. 4, 2009, claiming benefit of U.S. Provisional Application No. 60/236,301, filed Sep. 28, 2000, the contents of each of which are incorporated by reference herein.

FIELD OF THE INVENTION

This application relates to a method and compositions for chemosensitization and radiosensitization of cancer cells through administration of compositions, such as antisense oligonucleotides, which reduce the amount of TRPM-2 in the cells. The invention is of particular applicability to cancers such as renal cell carcinoma (RCC) which are resistant to chemo- and radiotherapy.

BACKGROUND OF THE INVENTION

Treatment of cancers by chemotherapy or radiotherapy frequently results in side effects because the therapy used is not specific to the cancer and kills non-cancerous cells as well. Where the cancer is resistant to the therapy, the dosage used must be increased, and the side effects become more pronounced. Thus, as a general principal, it would be desirable to be able to increase the sensitivity of cancer cells to chemotherapy and radiotherapy so that lower effective dosages could be employed.

Renal cell cancer (RCC) accounts for approximately 2% of adult carcinomas with over 30,000 new cases and 12,000 deaths per year in the United States. Motzer et al., *N. Engl. J. Med.* 335: 865-875 (1996). Estimates of annual new diagnoses of RCC have been increasing steadily. Motzer et al, supra; McLaughlin et al., *Semin. Oncol.* 27: 115-123 (2000). Despite extensive evaluation of many different treatment modalities, advanced metastatic RCC remains highly resistant to systemic therapy. To date, no chemotherapy is established for the treatment of advanced kidney cancer with objective response rates higher than 15% that justifies its use as a single agent. Yagoda et al., *Semin. Oncol.* 22: 42-60 (1995). Combinations of chemotherapy plus hormonal agents have been studied but likewise are ineffective and result in additive toxicity. Nearly half of all patients with RCC die within 5 years of diagnosis and 5-year-survival for those with metastatic disease is <10%. Motzer et al., *J. Urol.* 163: 408-417 (2000). Therefore, in order to improve survival, preclinical and clinical evaluation of new agents and treatment programs to identify improved antitumor activity are priorities in this resistant disease.

Bladder cancer is the second most common malignancy of the genitourinary tract, and the fourth or fifth leading cause of cancer-related deaths of men in Western industrialized countries. The prognosis of patients with invasive and/or metastatic bladder cancer is still extremely poor, despite recent therapeutic advances. Advanced bladder cancer is commonly treated with a cisplatin-based combination chemotherapy. However, which palliative efficacy has been observed, this efficiacy is limited due to de novo drug resistance or the development of the cellular drug-resistant phenotype during treatment. Thus, advances in the treatment of bladder cancer are desirable.

SUMMARY OF THE INVENTION

In accordance with the present invention it has been found that administration of antisense oligodeoxynucleotides (ODN) targeted against the testosterone-repressed prostate message-2 (TRPM-2) gene can reduce the expression of TRPM-2 and as a result enhance sensitivity of cancer cells to chemotherapeutic agents and to radiotherapy both in vitro and in vivo. Thus, in accordance with a first aspect of the invention, there is provided a method for increasing the sensitivity of cancer cells to a chemotherapeutic agent, comprising exposing cancer cells to the chemotherapeutic agent and an agent which reduces the amount of TRPM-2 in the renal cell cancer cells. There is further provided a method for treating cancer, comprising administering to an individual suffering from cancer a chemotherapeutic agent and an agent which reduces the amount of TRPM-2 in the cells. Compositions may be prepared for specific use in these methods,

DETAILED DESCRIPTION OF THE INVENTION

Figure 1:
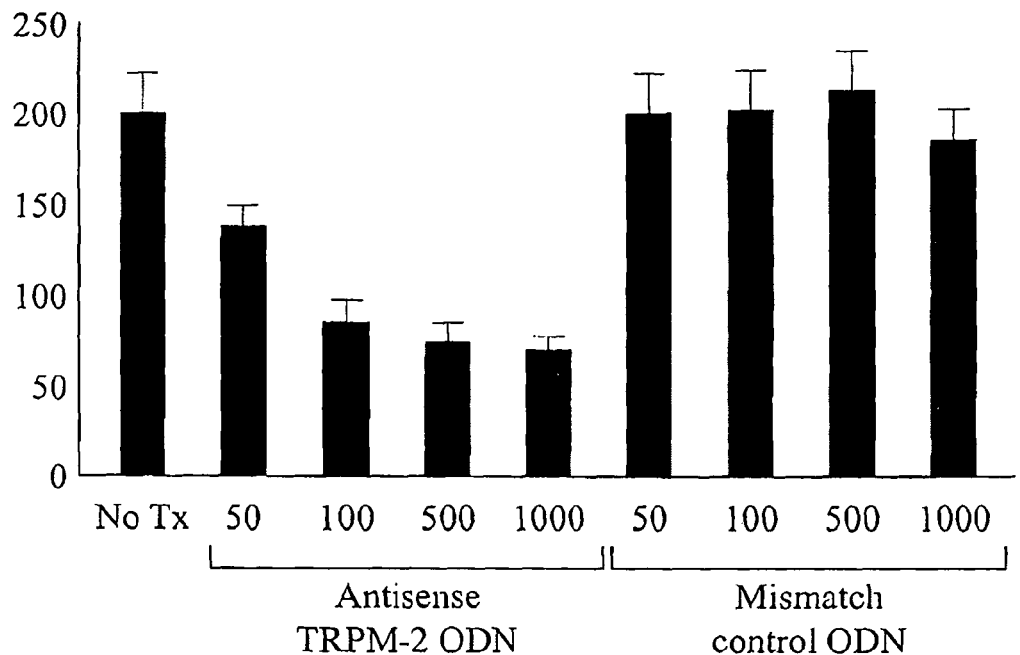
FIG. 1 shows sequence specific and dose-dependent downregulation of TRPM-2 in caki-2 cells in vitro.

The present invention provides a method and compositions for increasing the sensitivity of cancer cells to a chemotherapeutic agent, comprising exposing cancer cells to the chemotherapeutic agent and an agent which reduces the amount of TRPM-2 in the cancer cells. The compositions may be used in formulation of a pharmaceutical for use in increasing sensitivity of cancer to chemotherapeutic agents and radiation.

The present invention further provides a method for treating a cancer in which the cancer cells express TRPM-2, comprising administering to an individual suffering from the cancer a chemotherapeutic agent and art agent which reduces the amount of TRPM-2 in cancer cells of the individual. The two agents may be administered as part of a single composition or may be administered individually. In the latter case, the agent which reduces the amount of TRPM-2 may be administered before, at the same time as, or after the chemotherapy agent, provided that expression of TRPM-2 is reduced during at least a portion of the time that the chemotherapy agent is active.

Specific non-limiting examples of the types of cancer to which the invention may be applied include prostate cancer, renal cell carcinoma, bladder cancer, ovarian cancer and lung cancer.

As used in this application, the term "chemotherapy agent" refers to an agent which is added to cells or administered to an individual for the purpose of selectively killing cancerous cells. Examples of chemotherapy agents whose effectiveness may be enhanced using the method of the invention include but are not limited to taxanes (paclitaxel or docetaxel) and mitoxanthrone, cylcophosphamide, topoisomerase inhibitors, angiogenesis inhibitors, cisplatin-based therapies and differentiation agents and signal transduction inhibitors.

In the kidney, increased expression of TRPM-2 is observed in a number of acute and chronic states of renal injury and disease. However, little is known about changes of TRPM-2 expression levels in kidney cancer. Based on the analysis of only 4 patients, Parczyk et al reported a 3-fold overexpression of TRPM-2 in human renal cell cancer compared to normal kidney tissue. *J Cancer Res Clin Oncol* 120: 186-8 (1994).

In our study, reported in the examples below, we compared normal and malignant kidney tissues of 67 patients using TRPM-2-immunostaining. Our results confirm positive TRPM-2-staining in almost all RCC (98%) and increased TRPM-2 expression compared to normal tissue in a majority of RCC (61%). Sixty-six percent of normal kidney tissue samples distant from RCC did not or only weakly stained for TRPM-2, consistent with findings of other investigators. Parczyk et al, supra; Dvergsten et al., *Kidney International* 45: 828-35 (1994).

Overexpression of TRPM-2 in human prostate cancer LNCaP cells increases resistance to paclitaxel and other chemotherapies. Miyake et al., *Cancer Res* 60: 2547-54 (2000). Thus, in order to determine the functional role of increased TRPM-2 expression in RCC, we tested the effects of TRPM-2 antisense ODN on human Caki-2 RCC cell growth and whether TRPM-2 antisense ODN could enhance the cytotoxic effects of paclitaxel in this model system. Phosphorothioate TRPM-2 antisense ODN used in this study significantly inhibited expression of TRPM-2 mRNA in Caki-2 cells both in vitro and in vivo. Sequence specificity was confirmed using a 2-base TRPM-2 mismatch oligonucleotide, which had no effects on TRPM-2 expression in Caki-2 cells. When used alone, antisense or mismatch oligonucleotide treatment had no effect on Caki-2 cell growth. However, when administered in combination with other cell death stimuli, like cytotoxic chemotherapy, TRPM-2 antisense ODN enhanced Caki-2 cell apoptosis both in vitro and in vivo. Pretreatment of Caki-2 cells with TRPM-2 antisense ODN reduced the $IC_{50}$ of paclitaxel by 80%, thereby enhancing apoptosis induced by these agents. Consistent with these in vitro results, synergistic effects of combined use of TRPM-2 antisense ODN plus pactitaxel was also observed in vivo. Systemic administration of TRPM-2 antisense ODN plus polymeric micellar paclitaxel suppressed the Caki-2 tumor growth by 50%, compared to treatment with mismatch control oligonucleotides plus paclitaxel. Detection of increased apoptotic cells after combined antisense and chemotherapy by TUNEL staining in Caki-2 tumors suggest that decrease in tumor progression rates after combined TRPM-2 antisense ODN plus paclitaxel resulted from enhanced chemotherapy-induced apoptosis rather than decreased cell proliferation, although it is not Applicants' intention to be bound to this mechanism of action.

TRPM-2 expression levels were determined by Northern blot analysis in transitional cell carcinoma (TCC) of the bladder obtained from patients undergoing surgical treatment. Tests in a human bladder cancer cell line showed that treatment of the cells in vitro with TRPM-2 antisense increased the cytotoxic effect of cisplatin. In addition, synergistic inhibition of growth and metastasis of human bladder cancer tumors in athymic mice, in vivo, was observed.

As summarized in the examples below, similar results have been observed in tests on prostate cancer cells, ovarian cancer cells, and lung cancer cells. Thus, it appears that the invention is generally applicable to many cancer types, provided that the cancer cells have incressed levels of TRPM-2 expression/mRNA.

In the present invention, an agent is utilized which causes a reduction in the amount of TRPM-2 in treated cells, relative to untreated cells. While not intending to be bound by any particular mechanism, such a reduction may occur as a result of actual reductions in the amount of TRPM-2 produced from translation of mRNA, as a result of increases in the rate at which TRPM-2 is degraded, or as a result of reduction in the amount of TRPM-2 mRNA available for translation. The extent of the reduction should be sufficient to bring about an observable increase in the chemosensitivity of the treated renal cancer cells.

A suitable agent for reducing the amount of TRPM-2 is an antisense ODN, for example one which is 15-30 bases in length, which is complementary to the coding strand of portions of the TRPM-2 gene of the target cell. Table 1 shows representative antisense ODN sequences. Preferred antisense ODN sequences which are complementary to a region of the TRPM-2 mRNA spanning either the translation initiation site or the termination site. Specific preferred sequences are those shown in Seq. ID Nos. 4, 5 and 12.

TABLE 1

| Seq ID No. | Sequence |
|---|---|
| 1 | gcacagcaggagaatcttcat |
| 2 | gcacagcagcaggatcttcat |
| 3 | tggagtctttgcacgcctcgg |
| 4 | cagcagcagagtcttcatcat |
| 5 | attgtctgagaccgtctggtc |
| 6 | ccttcagctttgtctctgatt |
| 7 | agcagggagtcgatgcggtca |
| 8 | atcaagctgcggacgatgcgg |
| 9 | gcaggcagcccgtggagttgt |
| 10 | ttcagctgctccagcaaggag |
| 11 | aatttagggttcttcctggag |
| 12 | gctgggcggagttgggggcct |
| 13 | tctcccggcttgcgccat |
| 14 | tctcccggcatggtgcat |

The ODNs employed may be modified to increase the stability of the ODN in vivo. Far example, the ODNs may be employed as phosphorothioate derivatives (replacement of a non-bridging phosphoryl oxygen atoms with a sulfur atom) which have increased resistance to nuclease digestion, Administration of antisense ODNs can be carried out using the various mechanisms known in the art, including naked administration and administration in pharmaceutically acceptable Lipid carriers. For example, lipid carriers for antisense delivery are disclosed in U.S. Pat. Nos. 5,855,911 and 5,417,978 which are incorporated herein by reference. In general, the antisense is administered by intravenous, intraperitoneal, subcutaneous or oral routes.

The amount of antisense ODN administered is one effective to reduce the amount of TRPM-2 in cancer cells, and to thereby enhance the effectiveness of a chemotherapy agent being administered before, concurrently with or subsequent to the antisense ODN. It will he appreciated that this amount will vary both with the effectiveness of the antisense ODN employed, and with the nature of any carrier used. The determination of appropriate amounts for any given composition is within the skill in the art, through standard series of tests designed to assess appropriate therapeutic levels.

The invention will now be further described with reference to the following on-limiting examples:

EXAMPLE 1

TRPM-2 immunostaining was performed in normal kidney and RCC tissue of 67 patients. Histological classification of RCC revealed clear cell patterns in 56 cases (84.5%), the rest of sections showing either granular cell (6%) or papillary cell patterns (9%). Staining of cytoplasmic clusterin was heterogenous in both normal and malignant tissues. Positive TRPM-2-staining was found in almost all RCC (97%) and TRPM-2-overexpression, compared to normal tissue, was observed in most RCC (69%). (Table 2) Fifty-three percent of normal kidney tissue samples (distant from RCC) showed no or only weak staining for clusterin (Table 3).

TABLE 2

| % of tissue stained | normal kidney | RCC |
| --- | --- | --- |
| 0-25 | 50% | 21% |
| 25-50 | 28% | 27% |
| 50-75 | 19% | 30% |
| 75-100 | 3% | 22% |

TABLE 3

| Intensity of staining (arbitrary scoring) | normal kidney | RCC |
| --- | --- | --- |
| 0 | 17% | 3% |
| +1 | 37% | 12% |
| +2 | 37% | 49% |
| +3 | 9% | 22% |
| +4 | 0 | 14% |

EXAMPLE 2

The Caki-2 cell line derived from a human clear cell carcinoma of the kidney. It was purchased from the American Type Culture Collection (Rockville, Md.). Cells were maintained in McCoy's 5a medium (Life Technologies, Inc., Gaithersburg, Md.) supplemented with 10% heat-inactivated fetal calf serum.

Phosphorothioate TRPM-2 antisense ODN was made in accordance with the inventors instructions by La Jolla Pharmaceuticals Co. (La Jolla, Calif.). The sequence of TRPM-2 antisense ODN corresponding to the human TRPM-2 translation initiation site was 5'-CAGCAGCAGAGTCTTCAT-CAT-3' (Seq. ID No. 4). A two-base TRPM-2 mismatch oligonucleotide, 5'-CAGCAGCAGAGTATTTATCAT-3' (Seq. ID No. 15) was used as control.

Lipofectin, a cationic lipid (Life Technologies, Inc.) was used to increase oligonucleotide uptake of cells. Caki-2 cells were treated with various oligonucleotide concentrations after preincubation for 20 minutes with 20 µg/ml lipofectin in serum free OPTI-MEM (Life Technologies, Inc.). Four hours after the beginning of the incubation, the medium containing oligonucleotides and lipofectin was replaced with standard culture medium described above.

Total RNA was isolated from cultured Caki-2 cells using the acid-guanidium thiocyanate-phenol-chloro form method. Electrophoresis, hybridization and washing conditions were carried out as previously reported. Miyake et al., *Cancer Res* 59: 4030-4 (1999). Human TRPM-2 and glyceraldehyde-3-phosphate dehydrogenase (G3PDH) cDNA probes were generated by reverse transcription-PCR from total RNA of human kidney using primers 5-AAGGAAATTCAAAAT-GCTGTCAA-3' (sense, Seq ID No. 16) and 5'-ACAGACAA-GATCTCCCGGCACTT-3' (antisense, Seq. ID No. 17) for TRPM-2 , and 5'-TGCTTTTAACTCTGGTAAAGT-3' (sense, Seq. ID No. 18) and 5'-ATATTTGGCAG-GTTTTTCTGA-3' (antisense, Seq. ID No. 19) for G3PDH. Density of bands for TRPM-2 was normalized against that of G3PDH by densitometric analysis.

As shown in FIG. 1, treatment of Caki-2 cells with TRPM-2 antisense ODN (50, 100, 500 , or 1000 nM) for 2 days reduced TRPM-2 mRNA levels by 42%, 58%, 61%, and 64%, respectively, while TRPM-2 mRNA expression was not affected by mismatch control oligonucleotides at any of the employed concentrations.

EXAMPLE 3

Paclitaxel was purchased from Sigma Chemical Co. (St. Louis, Mo.). Stock solutions of paclitaxel were prepared with dimethyl sulfoxide (DMSO), and diluted with PBS to the required concentrations before each in vitro experiment. Polymeric micellar paclitaxel used in this study was generously supplied by Dr. Helen M. Burt (Faculty of Pharmaceutical Sciences, University of British Columbia, Vancouver, Canada), as previously reported. Leung et al., Prostate 44: 156-63 (2000).

Figure 2:
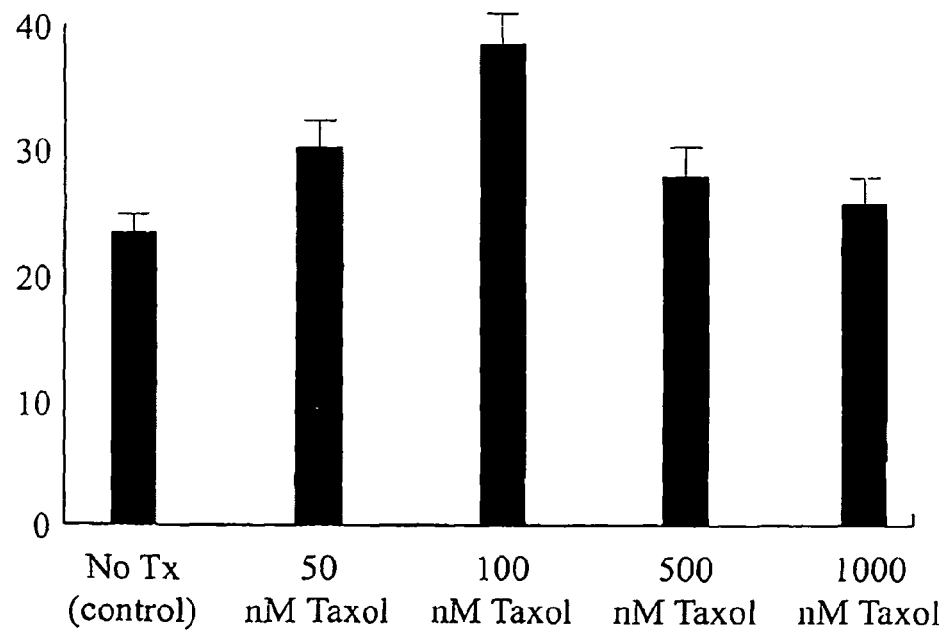
FIG. 2 shows TRPM-2 up-regulation in caki-2 cells, in vitro, after treatment h paclitaxel.

Northern blot analysis was used to assess the effects of paclitaxel treatment on TRPM-2 mRNA expression in Caki-2 cells in vitro and tumors in vivo, respectively. As shown in FIG. 2, TRPM-2 mRNA induction increased in a dose-dependent manner after paclitaxel treatment in vitro up to 73% at concentrations of 100 nM.

Figure 3:
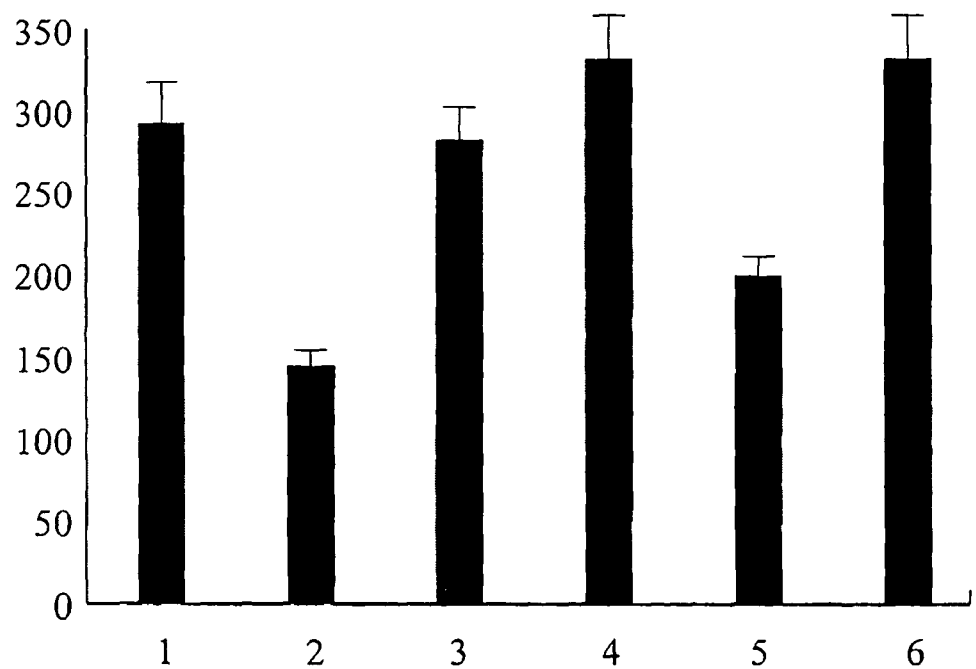
FIG. 3 shows TRPM-2 up-regulation in caki-2 cells, in vivo, after treatment with paclitaxel.

To determine whether paclitaxel changes TRPM-2 mRNA expression in Caki-2 tumors in vivo, 0.5 mg polymeric micellar paclitaxel was administered intravenously once daily over 10 days with harvest of tumors for mRNA extraction one day later. In nude mice bearing Caki-2 tumors, TRPM-2 mRNA levels increased by 15% atter treatment with paclitaxel compared to untreated control (FIG. 3).

EXAMPLE 4

To determine whether ASO treatment could reduce TRPM-2 expression in Caki-2 tumors in viva, tumor bearing nude mice were given 12.5 mg/kg TRPM-2 antisense ODN (Seq. ID No. 4) or mismatch control oligonucleotide (Seq ID No. 15) intraperitoneally once daily over 28 days with tumors harvested for mRNA-extraction one day later. Treatment with TRPM-2 antisense ODN resulted in a 51% reduction in TRPM-2 mRNA levels in Caki-2 tumors compared to mismatch control oligonucleotide-treated tumors.

EXAMPLE 5

Caki-2 cells were treated with 500 nM TRPM-2 antisense ODN (Seq ID No. 4) or mismatch control oligonucleotides (Seq. ID No. 15) once daily for two days and then incubated with medium containing various concentrations of paclitaxel for 2 days. The in vitro growth inhibitory effects of TRPM-2 antisense ODN plus paclitaxel on Caki-2 cells were assessed using the MTT assay as described by Miyake et al. *Cancer Res* 60: 2547-54 (2000). Briefly, $1 \times 10^4$ cells were seeded in each well of 96-well microtiter plates and allowed to attach overnight. Cells were then treated once daily with 500 nM antisense ODN for 2 days. Following anstisense ODN treatment, cells were treated with various concentrations of paclitaxel. After 48 h of incubation, 20 μl of 5 mg/ml MTT (Sigma Chemical Co.) in PBS was added to each well, followed by incubation for 4 h at 37° C. The formazan crystals were dissolved in DMSO. The optical density was determined with a microculture plate reader (Becton Dickinson Labware, Lincoln Park, N.J.) at 540 nm. Absorbance values were normalized to the values obtained for the vehicle-treated cells to determine the percentage of survival. Each assay was performed in triplicate.

Figure 4:
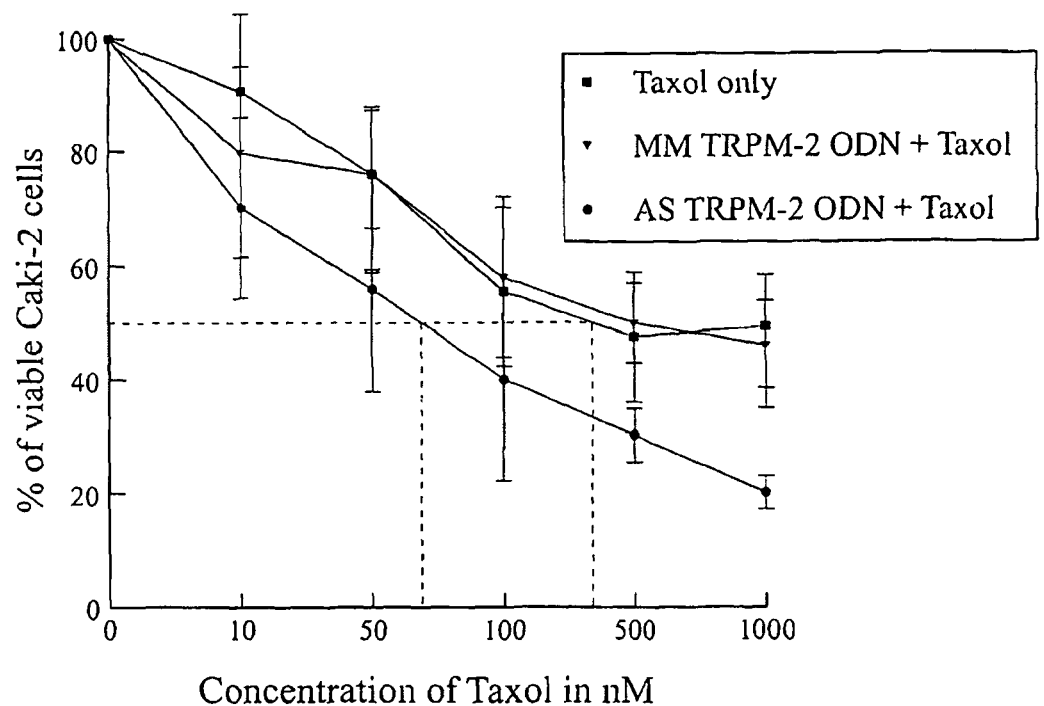
FIG. 4 shows chemosensitization of caki-2 cells, in vitro, after treatment with antisense TRPM-2 ODN.

As shown in FIG. 4, TRPM-2 antisense ODN treatment significantly enhanced chemosensitivity of paclitaxel in a dose-dependent manner (two-sided, P=0.022 , ANOVA), reducing the $IC_{50}$ (i.e., the concentration that reduces cell viability by 50%) of paclitaxel by 80% (320 nM to 65 nM), whereas mismatch control oligonucleotides had no effect. The combined effects between TRPM-2 antisense ODN and paclitaxel were synergistic (P<0.05), as determined by an analysis that utilized the fractional product method. Duska et al. *J Natl Cancer Inst* 91:1557-63 (1999).

DNA fragmentation assay was performed to compare induction of apoptosis after combined treatment with 500 nM TRPM-2 antisense ODN and 10 nM paclitaxel. The nucleosomal DNA degradation was analyzed as described previously with a minor modification. Briefly, $1 \times 10^5$ Caki-2 cells were seeded in 10 cm culture dishes and allowed to adhere overnight. After treatment with ASO plus paclitaxel using the same schedule as described above, cells were harvested and then lysed in a solution containing 100 mM NaCl, 10 nM Tris pH 7.4, 25 mM EDTA and 0.5% SDS. After centrifugation, supernatants were incubated with 300 μg/ml proteinase K for 5 h at 65° C. and extracted with phenol-chloroform. The aqueous layer was treated with 0.1 volume of 3 M sodium. acetate, and the DNA was precipitated with 2.5 volumes of 95% ethanol. Following treatment with 100 μg/ml RNAse A for 1 h at 37° C., the sample was electrophoresed on a 2% agarose gel and stained with ethidium bromide. After the same treatment schedule described above, characteristic apoptotic DNA laddering was observed only after combined treatment with TRPM-2 antisense ODN and paclitaxel.

EXAMPLE 6

Figure 5:
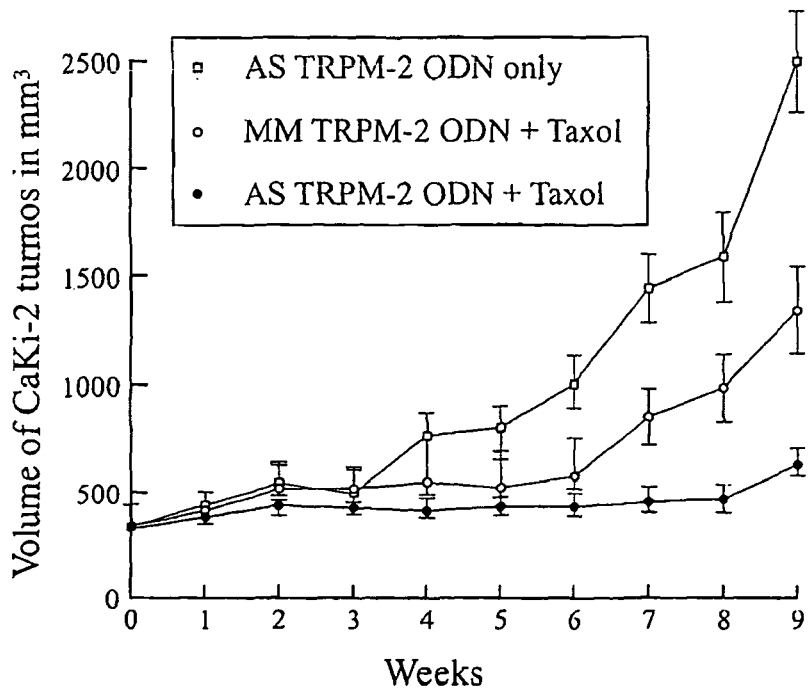
FIG. 5 shows chemosensitization of caki-2 cells, in vivo, after treatment with antisense TRPM-2 ODN.

Male athymic mice bearing Caki-2 tumors approximately 1 cm in diameter were randomly selected for treatment with TRPM-2 antisense ODN (Seq. ID No. 4) plus paclitaxel, mismatch control oligonucleotides (Seq. ID No. 15) plus paclitaxel, or TRPM-2 antisense ODN (Seq. ID No. 4) alone. Mean tumor volume was similar at the beginning of treatment in each of these groups (365-375 mm³). After randomization, 12.5 mg/kg TRPM-2 antisense ODN or mismatch control oligonucleotides were injected intraperitoneally once daily for 28 days. From day 10 to 14 , and from day 24 to 28, 0.5 mg polymeric micellar paclitaxel was administered once daily by intravenous injection. As shown in FIG. 5, TRPM-2 antisense ODN enhanced micellar paclitaxel chemosensitivity in Caki-2 tumors, causing a 50% reduction in mean tumor volume 7 weeks after initiation of treatment, compared to treatment with mismatch control oligonucleotides and paclitaxel (two-sided P<0.05). In vivo, the combined effects between TRPM-2 antisense ODN and paclitaxel were synergistic (P<0.05), as analyzed by the fractional product method. In addition, TUNEL staining detected a 3-fold increase in the numbers of apoptotic cells in Caki-2 tumors treated with TRPM-2 antisense ODN plus micellar paclitaxel (mean number of apoptotic cells/high power field: 11.6), compared to those treated with mismatch control oligonucleotides plus micellar paclitaxel (mean number of apoptotic cells/high power field: 4.1), or TRPM-2 antisense ODN alone (mean number of apoptotic cells/high power field: 2.3).

Under the experimental conditions used in the above in vivo experiments, no side effects associated with antisense treatment and/or chemotherapy were observed (except one animal developing ascites, 3 weeks after TRPM-2 antisense ODN treatment was finished).

EXAMPLE 7

Figure 8:
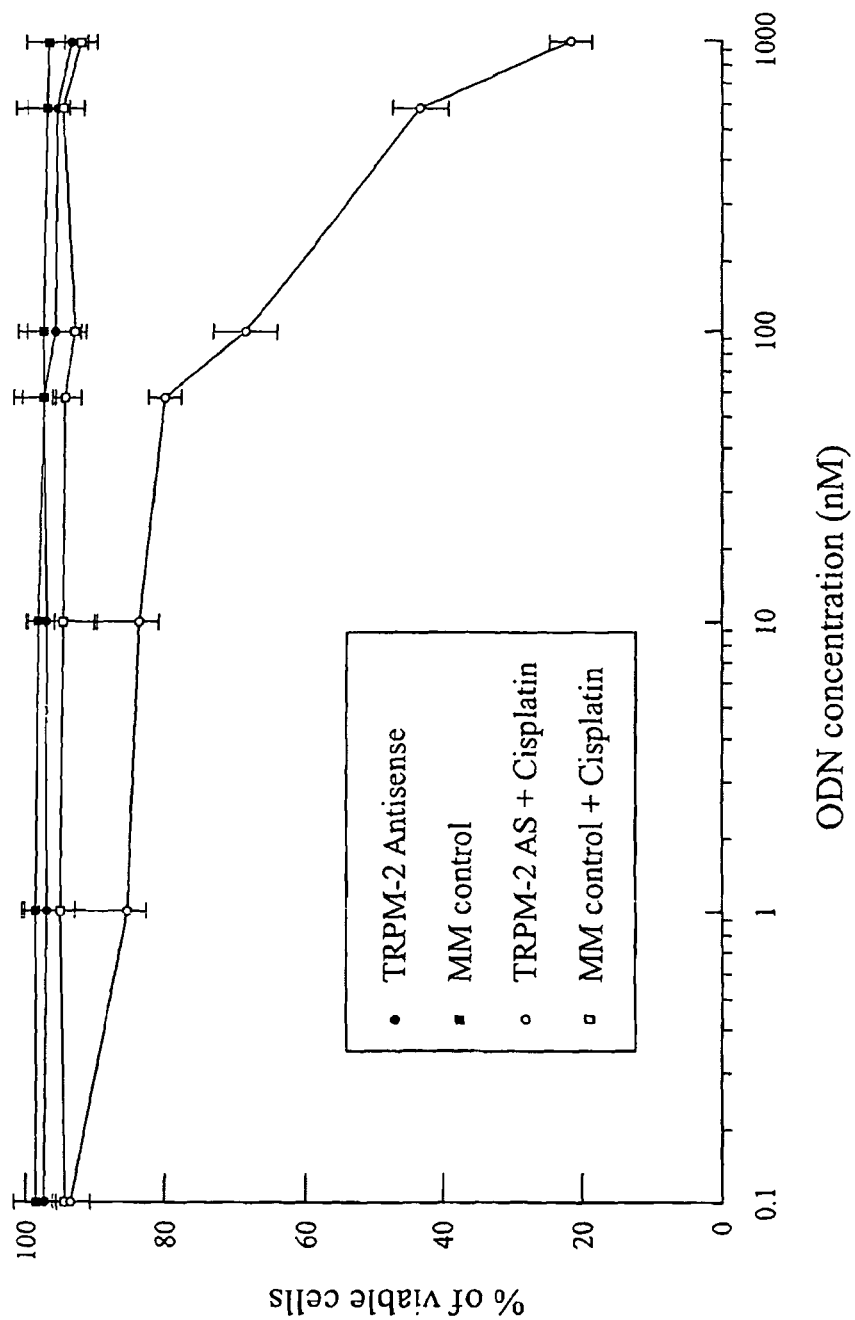
FIG. 8 shows reduction in cell viability for KoTCC-1 (bladder cancer) cells treated with a combination of TRPM-2 antisense and cisplatin.

Antisense TRPM-2 ODNs enhance radiation sensitivity of cancer cells which express TRPM-2. Using northern analysis, we found that radiation therapy results in dose and time dependent increases in TRPM2 gene expression in human prostate cancer PC-3 cells (FIG. 8). Overexpression of TRPM2 results in increased resistance to radiation induced cell death. Human prostate LNCaP cells that overexpress TRPM2 (LNCaP/T1) are more resistant to radiation therapy (FIGS. 9A and B). Treatment of human prostate cancer PC-3 cells with 100 and 500 nM antisense TRPM-2 ODNs (Seq. ID. NO. 1) significantly reduces cell survival after a single treatment of 4 Gy radiation therapy compared to mismatch ODN (Seq. ID No. 2) treatment. (FIG. 10). FIGS. 11A and B show dose dependent radiation sensitization of human prostate cancer PC-3 cells after treatment with 10, 50 , and 100 nM antisense TRPM-2 oligo in vitro.

EXAMPLE 8

To determine whether treatment with human antisense TRPM-2 ODN enhances chemosensitivity in the PC3 human prostate cancer cell line, mice bearing PC3 tumors were treated with antisense human TRPM-2 ODN plus micellar paclitaxel or mitoxantrone, and mismatch control ODN plus micellar paclitaxel or mitoxantrone (FIGS. 12A and 12B). ODN was administered for 28 days and either 0.5 rag micellar taxol or 0.3 mg mitoxantrone were administered on two occasions: from day 10 to 14 , and day 24 to 28. A significant reduction in tumor size was observed in the antisense ODN treated animals as compared to those treated with mismatch control ODN. This effect was even more pronounced after the second dosing of the micellar paclitaxel or mitoxantrone.

EXAMPLE 9

Figure 6:
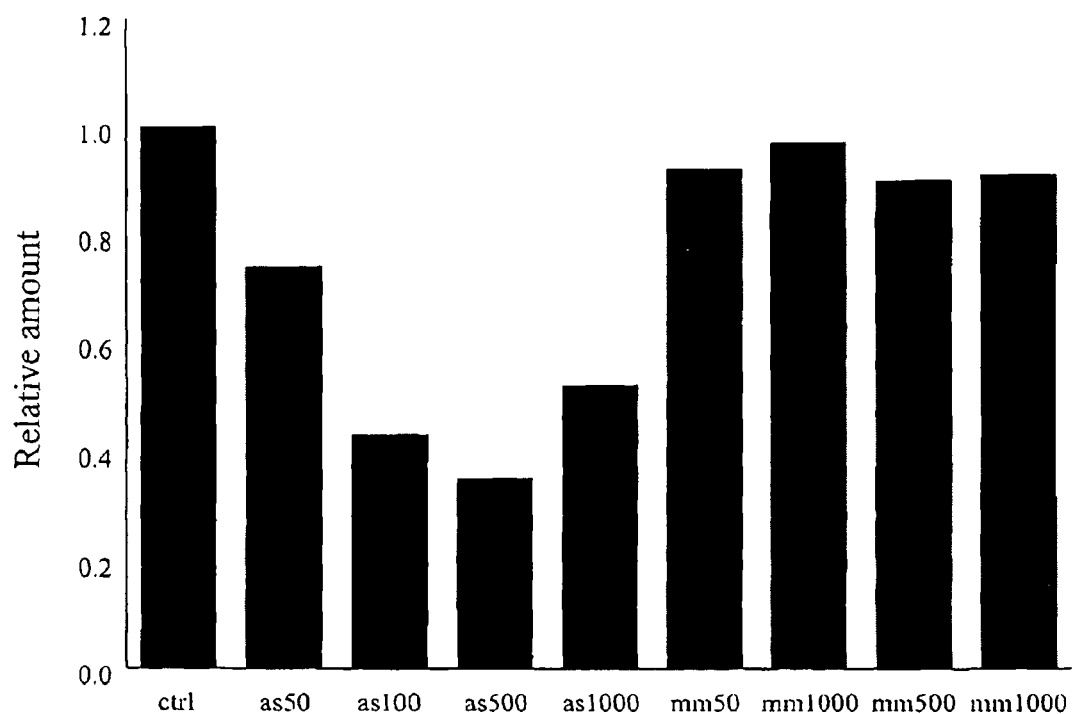
FIG. 6 shows the amount of TRPM-2 mRNA in ovarian cancer cells after treatment with differing amount of TRPM-2 antisense (AS) or mismatch control (MM). The number in each case reflects the concentration of the oligonucleotide in nanomolar units.

An ovarian cancer cell line (OVCAR3) was treated with different amounts of TRPM-2 antisense (Seq. ID 4) or mismatch oligonucleotide (Seq. ED. No. 15) using OligofectAMINE™ as a carrier and the amount of TRPM-2 mRNA was determined after 2 days using Northern blot analysis as described above. The results are summarized in FIG. 6. As shown, there is a substantially dose-dependent reduction in TRPM-2 mRNA levels using the TRPM-2 antisense, but no reduction in the absence of oligonucleotide (ctrl) or using the mismatch control oligonucleotide. The same results were observed in using real time PCR to determine the amount of TRPM-2 mRNA.

Tissue sections of cancer ovarian tissue, before and after chemotherapy with taxol, and of normal ovarian tissue were observed microscopically after immunohistochemical staining specific for TRPM-2. Increased TRPM-2 levels were observed in the post-chemotherapy sections, although no obvious difference was seen between normal ovary and pre-chemotherapy cancerous tissue. Thus, expression of TRPM-2 may provide a defense for ovarian cancer cells against chemotherapeutic treatment.

EXAMPLE 10

A lung cancer cell line (A549) was treated with different concentrations (50-1000 nM) of TRPM-2 antisense (Seq. ID No. 4) or mismatch oligonucleotide (Seq. ID. No. 15) and evaluated by Northern blot analysis as described above. Dose-dependent and sequence specific down-regulation of TRPM-2 mRNA levels was observed. Combination treatments of A549 cells with paclitaxel (0-50 nM) and either TRPM-2 antisense (Seq. ID No. 4) or mismatch control (Seq. ID No, 15) (0 or 500 nM) were analyzed as described in Example 6. Characteristic apoptotic DNA laddering was observed only after combined treatment with TRPM-2 antisense ODN and paclitaxel.

Figure 7:
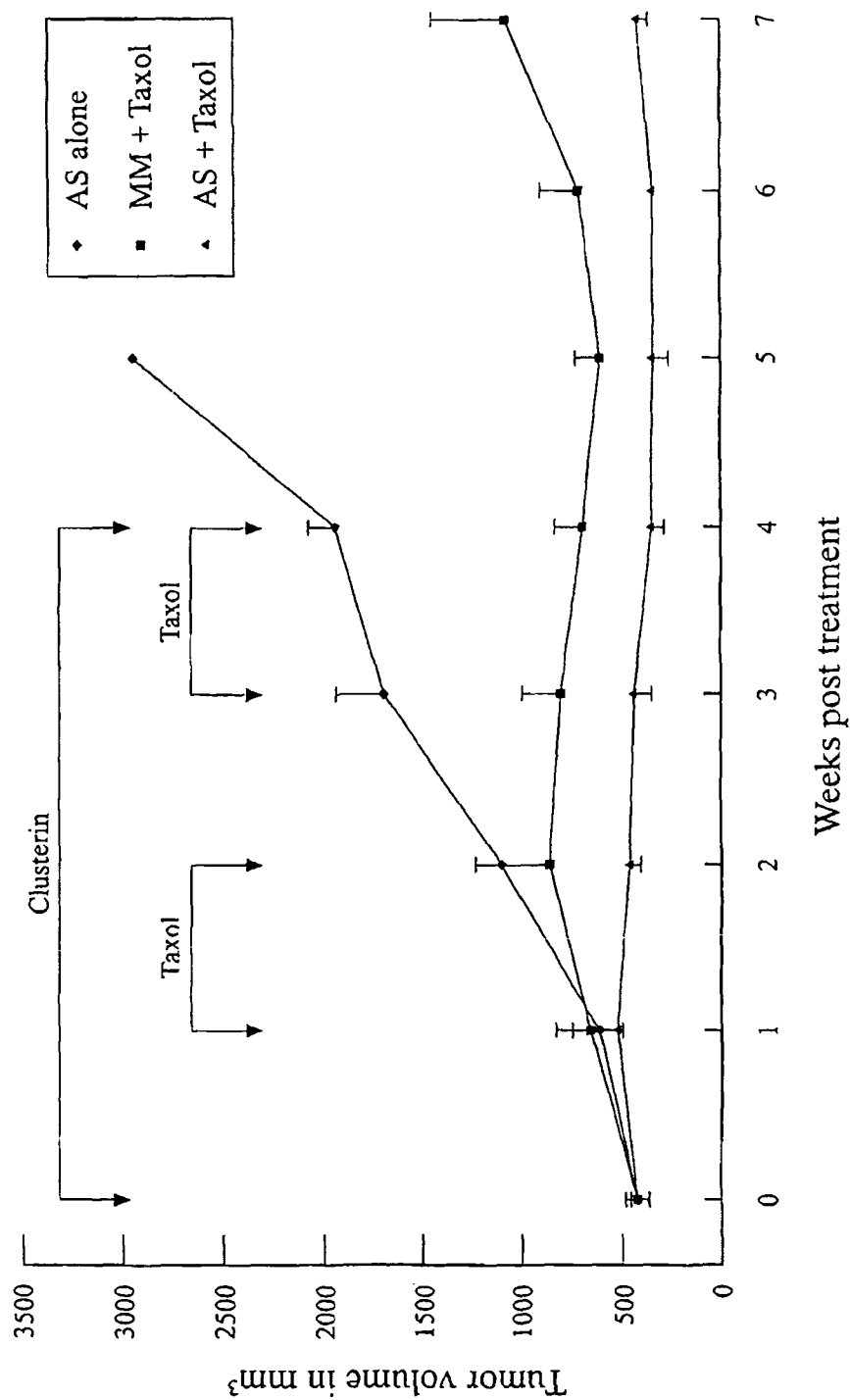
FIG. 7 shows combined effect of TRPM-2 antisense and taxol on A549 tumors (lung) in SCID mice.

A549 tumors were introduced into SCID mice using standard protocols. Mice were treated with TRPM-2 antisense (Seq. ID. No. 4) alone, or a combination of taxol with the TRPM-2 antisense or mismatch control (Seq. ID. No. 15). Tumor volume was measured periodically. The results are summarized in FIG. 7. As shown, the combination of the TRPM-2 antisense provides improved control over tumor volume.

EXAMPLE 11

ACHN, a cell line derived from human RCC, was purchased from the American Type Culture Collection. pRC-CMV expression vector containing the 1.6 kb cDNA fragment encoding human TRPM-2 was provided by Dr. Martin Tenniswood (W. Alton Jones Cell Science Center, Lake Placid, N.Y.). The expression vector was transfected into ACTIN cells by the liposome-mediated gene transfer method. Miyake et al., Cancer Res. 60: 170-176 (2000) to generate ACHN cell overexpressing TRPM-2. TRPM-2 expression was detected in four independent cell lines (ACHN/CL#1-4), but not in the parental cell line (ACHN/P) or the vector-only transfected control (ACHN/Co).

In vitro growth rates were determined for ACHN/P, ACHN/Co, ACHN/CL#1 and ACHN/CL#2 using the MTT assay described above. No significant difference in cell proliferation was observed among the cell ines. These same four cell ines were exposed to cisplatin in vitro. ACHN/CL#1 and ACHN/CL2 acquired resistance to cisplatin in comparison with ACHN/P and ACHN/Co. Overpexression of TRPM-2 in ACHN cells increased the $IC_{50}$ of cisplatin more than 5-fold.

Induction of apoptosis in ACHN sublines treated with 10 mg/ml cisplatin for 72 hours was assessed by DNA degradation assay and Western blot analysis of PARP prpotein, a substrate for caspases activated during the process of apoptotic execution. Characteristic apoptotic DNA ladders were detected in ACHN/P and ACHN/Co but not in ACHN/CL#1 or ACHN/CL#2 indicating the protective effect of TRPM-2 overexpression.

To examine the in vivo effect of TRPM-2 expression on tumor growth, $5 \times 10^6$ cells of each cell line were injected subcutaneously into the flank of athymic nude mice. There were no significant different in tumor growth amoung ACHN/P, ACHN/Co, ACHN/CL#1 and ACHN/CL#2 , that is TRPM-2 overexpression did not stimulate a proliferative potential of ACHN in vivo.

Four weeks after tumor cell injection, 50 μg/mouse of cisplatin was injected intravenously twice a week for two weeks. Sixty days after injection of the tumor cells, ACHN/CL#1 and ACHN/CL#2 formed tumors twice as large as those formed by ACHN/P and ACHN/Co.

EXAMPLE 12

The human bladder cancer cell line KoTCC-1 has been described previously. Miyake et al. *J. Urol*. 157: 2351-2355 (1997). KoTCC-1 cells were treated in vitro with TRPM-2 antisense (Seq. ID. No. 4) or a mismatch control (Seq. ID. No. 15) at concentrations of 100, 500 or 1000 nM daily for two days. Northern blot analysis was performed as described above. TRPM-2 antisense reduced the amount of TRPM-2 antisense in a sequence-specific dose dependent manner (22, 59 or 95%). Inhibition of TRPM-2 protein levels was observed by Western blot analysis after daily treatment with the TRPM-2 antisense for 4 consecutive days.

Northern blot analaysis was used to determine the effect of cisplatin treatment on TRPM-2 mRNA levels in KoTCC-1 cells. TRPM-2 mRNA induction increased in a dose-dependent manner by ciplatin treatments at concentrations up to 10 mg/ml. Time course experiments demonstrated that cisplatin-induced TRPM-2 mRNA up-regulation peaked by 48 hours posttreatments and began decreasing by 96 hours posttreatment.

Combined treatment with 500 nM TRPM-2 antisense (Seq. ID. No 4) and 5 mg/ml or 10 mg/ml cisplatin decreased TRPM-2 mRNA levels by 81% or 76%, respectively, as compared to 500 nM mismatch control (Seq. ID No. 15).

KoTCC-1 cells were treated in vitro with 500 nM TRPM-2 antisense (Seq. ID. No. 4) or mismatch control (Seq. ID. No. 15) once daily for two days and then incubated with medium containing various concentrations of cisplatin for 2 days. The MTT assay was performed to determine cell viability. TRPM-2 antisense was shown to reduce the $IC_{50}$ of cisplatin by more than 50%. Dose-dependent synergy was also observed by increasing the amount of antisense when the cisplatin concentration was fixed at 10 mg/ml. (FIG. 8)

EXAMPLE 13

The efficacy of a treatment regimen combining TRPM-2 antisense and cisplatin for inhibiting growth of subcutaneous KoTCC-1 tumors in athymic nude mice was evaluated. Mice with tumors approximately 1 cm in diameters were treated with TRPM-2 antisense (Seq. ID. No. 4) alone (10 mg/kg, ip, once daily in each mouse for 28 days), mismatch control (Seq. ID. No. 15) alone (10 mg/kg, ip, once daily in each mouse for 28 days), TRPM-2 antisense (10 mg/kg, ip, once daily in each mouse for 28 days) and cisplatin (50 μg iv twice a week for two weeks) or mismatch control (10 mg/kg, ip, once daily in each mouse for 28 days) and cisplatin (50 μg iv twice a week for two weeks). Mean tumor volumes were measured weekly. The result arc shown in FIG. 9.

A modified TUNEL technique was used to detect apoptotic cells in KoTCC cells treated with TRPM-2 antisense and cisplatin. A 6-, 6- and 3-fold increase in the number of apoptotic cells was detected for the combination of TRPM-2 antisense and cisplatin, relative to TRPM-2 antisense alone, mismatch control alone or mismatch control and cisplatin, respectively.

The invention claimed is:

1. A method for treating an individual suffering from ovarian cancer comprising administering to said individual a therapeutically effective amount of an antisence oligonucleotide and chemotherapy comprising a taxane, wherein the antisence oligonucleotide has nucleotides in the sequence set forth in Seq. ID No. 4 and which antisense oliglnucleotide comprises a phosphorothioate modification to increase the stability thereof in vivo, and wherein the antisense oligonucleotide is administered to said individual before and after the chemotherapy such that the expression of testosterone-repressed prostate message-2 (TRPM-2) is reduced during at least a portion of the time that the taxane is active, thereby treating said individual.

2. A method for enhancing chemosensitivity in an individual suffering from ovarian cancer comprising administering to said individual a therapeutically effective amount of an antisense oligonucleotide and chemotherapy comprising a taxane, wherein the antisense oligonucleotide has nucleotides in the sequence set forth in Seq. ID No. 4 and which antisense oligonucleotide comprises thereof in vivo, and wherein the antisense oligonucleotide is administered to said individual before and after the chemotherapy such that the expression of testosterone-repressed prostate message-2 (TRPM-2) is reduced during at least a portion of the time that the taxane is active, thereby enhancing chemosenseitivity in said individual.

3. The method for treating an individual suffering from bladder cancer comprising administering to said individual a therapeutically effective amount of an antisense oligonucleotide and chemotharpy comprising a taxane, wherein the antisense oligonucleotide has nucleotides in the sequence set forth in seq. ID No. 4 and which antisense oligonucleotide comprises a phosphorothioate modification to increase the stability thereof in vivo, and wherein the antisense oligonucleotide is administered to said individual before and after the chemotherapy such that the expression of testosterone-repressed prostate message-2 (TRPM-2) is reduced during at least a portion of the time that the taxane is active, thereby treating said individual.

4. A method for enhancing chemosensitivity in an individual suffering from bladder cancer comprising administering to said individual a therapeutically effective amount of an antisense oligonucleotide and chemotherapy comprising a taxane, wherein the antisense oligonucleotide has nucleotides in the sequence set forth in seq. ID No. 4 and which antisense oligonucleotide comprises a phosphorothioate modification to increase the stability thereof in vivo, and wherein the antisense oligonucleotide is administered to said individual before and after the chemotherapy such that the expression of testosterone-repressed prostate message-2 (TRPM-2) is reduced during at least a portion of the time that the taxane is active, thereby enhancing chemosensitivity in said individual.

5. The method of claim 1, wherein the taxane is docetaxel.
6. The method of claim 1, wherein the taxane is paclitaxel.
7. The method of claim 2, wherein the taxane is docetaxel.
8. The method of claim 2, wherein the taxane is paclitaxel.
9. The method of claim 3, wherein the taxane is docetaxel.
10. The method of claim 3, wherein the taxane is paclitaxel.
11. The method of claim 4, wherein the taxane is docetaxel.
12. The method of claim 4, wherein the taxane is paclitaxel.

* * * * *

UNITED STATES PATENT AND TRADEMARK OFFICE
CERTIFICATE OF CORRECTION

| | | |
|---|---|---|
| PATENT NO. | : 9,095,602 B2 | Page 1 of 1 |
| APPLICATION NO. | : 13/737630 | |
| DATED | : August 4, 2015 | |
| INVENTOR(S) | : Gleave et al. | |

It is certified that error appears in the above-identified patent and that said Letters Patent is hereby corrected as shown below:

In the Claims,

In Column 15, Claim 1, Lines 2-7 should read, "A method for treating an individual suffering from ovarian cancer comprising administering to said individual a therapeutically effective amount of an antisense oligonucleotide and chemotherapy comprising a taxane, wherein the antisense oligonucleotide has nucleotides in the sequence set forth in Seq. ID No. 4 and which antisense oligonucleotide..."

In Column 15, Claim 2, Lines 21-27 should read, "...oligonucleotide comprises a phosphorothioate modification to increase the stability thereof in vivo, and wherein the antisense oligonucleotide is administered to said individual before and after the chemotherapy such that the expression of testosterone-repressed prostate message-2 (TRPM-2) is reduced during at least a portion of the time that the taxane is active, thereby enhancing chemosensitivity in said individual."

In Column 15, Claim 3, Lines 28-31 should read, "A method for treating an individual suffering from bladder cancer comprising administering to said individual a therapeutically effective amount of an antisense oligonucleotide and chemotherapy comprising a taxane, wherein the..."

Signed and Sealed this
Fifteenth Day of December, 2015

Michelle K. Lee
*Director of the United States Patent and Trademark Office*

```
                              SEQUENCE LISTING

<160> NUMBER OF SEQ ID NOS: 15

<210> SEQ ID NO 1
<211> LENGTH: 21
<212> TYPE: DNA
<213> ORGANISM: human

<400> SEQUENCE: 1
gcacagcagg agaatcttca t                                                   21

<210> SEQ ID NO 2
<211> LENGTH: 21
<212> TYPE: DNA
<213> ORGANISM: human

<400> SEQUENCE: 2
gcacagcagc aggatcttca t                                                   21

<210> SEQ ID NO 3
<211> LENGTH: 21
<212> TYPE: DNA
<213> ORGANISM: human

<400> SEQUENCE: 3
tggagtcttt gcacgcctcg g                                                   21

<210> SEQ ID NO 4
<211> LENGTH: 21
<212> TYPE: DNA
<213> ORGANISM: human

<400> SEQUENCE: 4
cagcagcaga gtcttcatca t                                                   21

<210> SEQ ID NO 5
<211> LENGTH: 21
<212> TYPE: DNA
<213> ORGANISM: human

<400> SEQUENCE: 5
attgtctgag accgtctggt c                                                   21

<210> SEQ ID NO 6
<211> LENGTH: 21
<212> TYPE: DNA
<213> ORGANISM: human

<400> SEQUENCE: 6
ccttcagctt tgtctctgat t                                                   21

<210> SEQ ID NO 7
<211> LENGTH: 21
<212> TYPE: DNA
<213> ORGANISM: human

<400> SEQUENCE: 7
agcagggagt cgatgcggtc a                                                   21

<210> SEQ ID NO 8
<211> LENGTH: 21
```

```
<212> TYPE: DNA
<213> ORGANISM: human

<400> SEQUENCE: 8
atcaagctgc ggacgatgcg g                                              21

<210> SEQ ID NO 9
<211> LENGTH: 21
<212> TYPE: DNA
<213> ORGANISM: human

<400> SEQUENCE: 9
gcaggcagcc cgtggagttg t                                              21

<210> SEQ ID NO 10
<211> LENGTH: 21
<212> TYPE: DNA
<213> ORGANISM: human

<400> SEQUENCE: 10
ttcagctgct ccagcaagga g                                              21

<210> SEQ ID NO 11
<211> LENGTH: 21
<212> TYPE: DNA
<213> ORGANISM: human

<400> SEQUENCE: 11
aatttagggt tcttcctgga g                                              21

<210> SEQ ID NO 12
<211> LENGTH: 21
<212> TYPE: DNA
<213> ORGANISM: human

<400> SEQUENCE: 12
gctgggcgga gttgggggcc t                                              21

<210> SEQ ID NO 13
<211> LENGTH: 18
<212> TYPE: DNA
<213> ORGANISM: human

<400> SEQUENCE: 13
tctcccggct tgcgccat                                                  18

<210> SEQ ID NO 14
<211> LENGTH: 18
<212> TYPE: DNA
<213> ORGANISM: human

<400> SEQUENCE: 14
tctcccggca tggtgcat                                                  18

<210> SEQ ID NO 15
<211> LENGTH: 21
<212> TYPE: DNA
<213> ORGANISM: Artificial
<220> FEATURE:
<223> OTHER INFORMATION: 2 base mismatch primer from human TRPM-2

<400> SEQUENCE: 15
cagcagcaga gtatttatca t                                              21
```